United States Patent
Pond, Jr. et al.

(10) Patent No.: US 7,465,306 B2
(45) Date of Patent: Dec. 16, 2008

(54) SYSTEM AND METHOD FOR POSITIONING A CONNECTING MEMBER ADJACENT THE SPINAL COLUMN IN MINIMALLY INVASIVE PROCEDURES

(75) Inventors: John D. Pond, Jr., Germantown, TN (US); Anthony J. Melkent, Memphis, TN (US); Stephen Stamps, Memphis, TN (US); Luke Perkins, Memphis, TN (US)

(73) Assignee: Warsaw Orthopedic, Inc., Warsaw, IN (US)

( * ) Notice: Subject to any disclaimer, the term of this patent is extended or adjusted under 35 U.S.C. 154(b) by 465 days.

(21) Appl. No.: 10/918,835

(22) Filed: Aug. 13, 2004

(65) Prior Publication Data

US 2006/0036255 A1      Feb. 16, 2006

(51) Int. Cl.
*A61B 17/90* (2006.01)
(52) U.S. Cl. .................. 606/86 A; 606/265; 606/96; 606/104
(58) Field of Classification Search .............. 606/61, 606/86
See application file for complete search history.

(56) References Cited

U.S. PATENT DOCUMENTS

| | | | |
|---|---|---|---|
| 2,338,159 A | 1/1944 | Appleton | |
| 4,246,660 A * | 1/1981 | Wevers | ............ 623/13.13 |
| 4,335,715 A | 6/1982 | Kirkley | |
| 4,545,374 A | 10/1985 | Jacobson | |
| 4,573,448 A | 3/1986 | Kambin | |
| 4,722,331 A | 2/1988 | Fox | |
| 4,883,048 A | 11/1989 | Purnell et al. | |
| 4,896,661 A | 1/1990 | Bogert et al. | |
| 4,955,885 A | 9/1990 | Meyers | |
| 5,163,940 A | 11/1992 | Bourque et al. | |
| 5,242,443 A | 9/1993 | Kambin | |
| 5,242,444 A | 9/1993 | MacMillan | |
| 5,281,223 A | 1/1994 | Ray | |
| 5,334,205 A | 8/1994 | Cain | |
| 5,383,454 A | 1/1995 | Bucholz | |
| 5,437,667 A | 8/1995 | Papierski et al. | |

(Continued)

FOREIGN PATENT DOCUMENTS

DE     100 27 988 A1     1/2002

(Continued)

OTHER PUBLICATIONS

Sofamor Danek; *The Spine Specialist TSRH Pedicle Screw Spinal System, Severe Spondylolisthesis of L5-Si Grade 3 & 4*; Surgical Technnique as described by Edward H. Simmons, MD, Edward D. Simmons, Jr. MD, Howard D. Markowitz, MD © 1997.

(Continued)

*Primary Examiner*—Eduardo C Robert
*Assistant Examiner*—Jerry Cumberledge
(74) *Attorney, Agent, or Firm*—Krieg Devault

(57) ABSTRACT

A spinal surgical system includes at least two extenders extending proximally from respective ones of first and second anchors engaged to the spinal column. A connecting member is positionable between the at least two extenders such that the connecting member extends between the at least two extenders. The connecting member is movable distally along the at least two extenders and engageable to the first and second anchors.

11 Claims, 25 Drawing Sheets

U.S. PATENT DOCUMENTS

| | | | |
|---|---|---|---|
| 5,569,248 | A | 10/1996 | Mathews |
| 5,591,165 | A | 1/1997 | Jackson |
| 5,591,167 | A | 1/1997 | Laurain et al. |
| 5,601,562 | A | 2/1997 | Wolf et al. |
| 5,613,971 | A | 3/1997 | Lower et al. |
| 5,643,273 | A | 7/1997 | Clark |
| 5,681,320 | A | 10/1997 | McGuire |
| 5,704,937 | A | 1/1998 | Martin |
| 5,720,751 | A * | 2/1998 | Jackson ............ 606/86 |
| 5,725,532 | A | 3/1998 | Shoemaker |
| 5,735,857 | A | 4/1998 | Lane |
| 5,741,266 | A | 4/1998 | Moran et al. |
| 5,752,962 | A | 5/1998 | D'Urso |
| 5,772,594 | A | 6/1998 | Barrick |
| 5,851,183 | A | 12/1998 | Bucholz |
| 5,871,445 | A | 2/1999 | Bucholz |
| 5,891,034 | A | 4/1999 | Bucholz |
| 5,891,150 | A | 4/1999 | Chan |
| 5,891,158 | A | 4/1999 | Manwaring et al. |
| 5,910,141 | A | 6/1999 | Morrison et al. |
| 6,036,692 | A | 3/2000 | Burel et al. |
| 6,099,528 | A | 8/2000 | Saurat |
| 6,123,707 | A | 9/2000 | Wagner |
| 6,183,472 | B1 | 2/2001 | Lutz |
| 6,226,548 | B1 | 5/2001 | Foley et al. |
| 6,235,028 | B1 * | 5/2001 | Brumfield et al. ............ 606/53 |
| 6,440,133 | B1 | 8/2002 | Beale et al. |
| 6,530,929 | B1 | 3/2003 | Foley et al. |
| 6,613,091 | B1 * | 9/2003 | Zdeblick et al. ......... 623/17.16 |
| 7,004,947 | B2 * | 2/2006 | Shluzas et al. ............ 606/105 |
| 7,160,300 | B2 * | 1/2007 | Jackson ............... 606/61 |
| 2002/0020255 | A1 | 2/2002 | Simon et al. |
| 2002/0045904 | A1 | 4/2002 | Fuss et al. |
| 2002/0161368 | A1 | 10/2002 | Foley et al. |
| 2003/0060826 | A1 * | 3/2003 | Foley et al. .................. 606/61 |
| 2003/0073998 | A1 | 4/2003 | Pagliuca et al. |
| 2004/0039384 | A1 | 2/2004 | Boehm, Jr. et al. |
| 2004/0138662 | A1 | 7/2004 | Landry et al. |
| 2004/0143265 | A1 | 7/2004 | Landry et al. |
| 2004/0147928 | A1 | 7/2004 | Landry et al. |

FOREIGN PATENT DOCUMENTS

| | | |
|---|---|---|
| EP | 1 374 786 A2 | 1/2004 |
| EP | 1 574 175 A1 | 9/2005 |
| SU | 0839513 | 6/1981 |
| WO | WO 97/38639 | 10/1997 |
| WO | WO 99/15097 | 4/1999 |
| WO | WO 99/26549 | 6/1999 |
| WO | WO 00/44288 | 8/2000 |
| WO | WO 2005/072081 A2 | 8/2005 |

OTHER PUBLICATIONS

Sofamor Danek, The Spine Specialist; *Horizon Spinal System, Surgical Technique*; as described by Samuel J. Laufer, M.D., J. Andrew Bowe, M.D. © 1999.

Posterior Percutaneous Spine Insturmentation; 9 Supp 1) Eur Spine J (2000) Received Sep. 3, 1999 Accepted Sep. 4, 1999.

Medtronic Sofamor Danek, *CD Horizon SEXTANT Rod Insertion System Surgical Technique*, as described by Kevin T. Foley, M.D., © 2002.

* cited by examiner

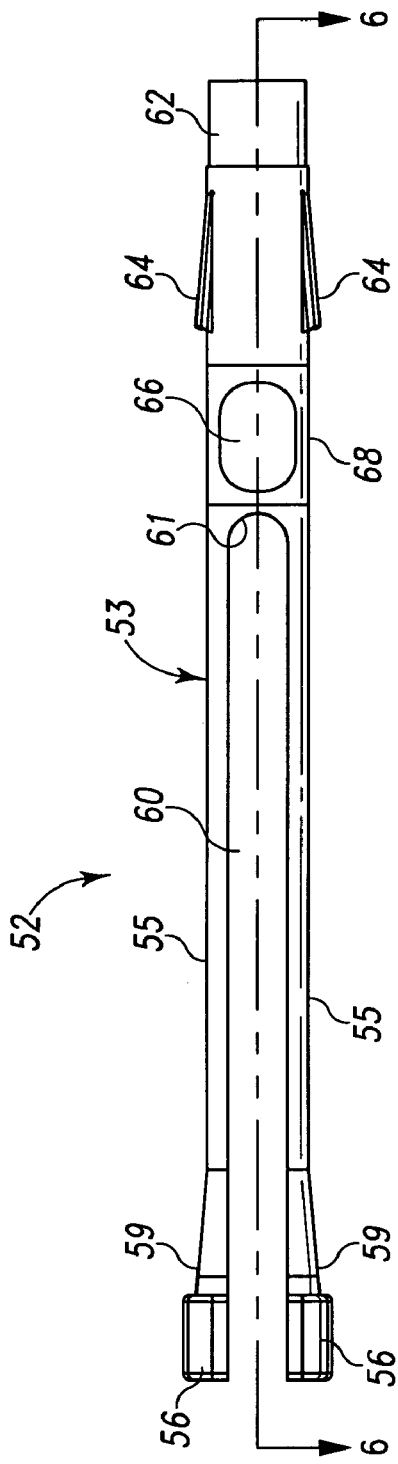
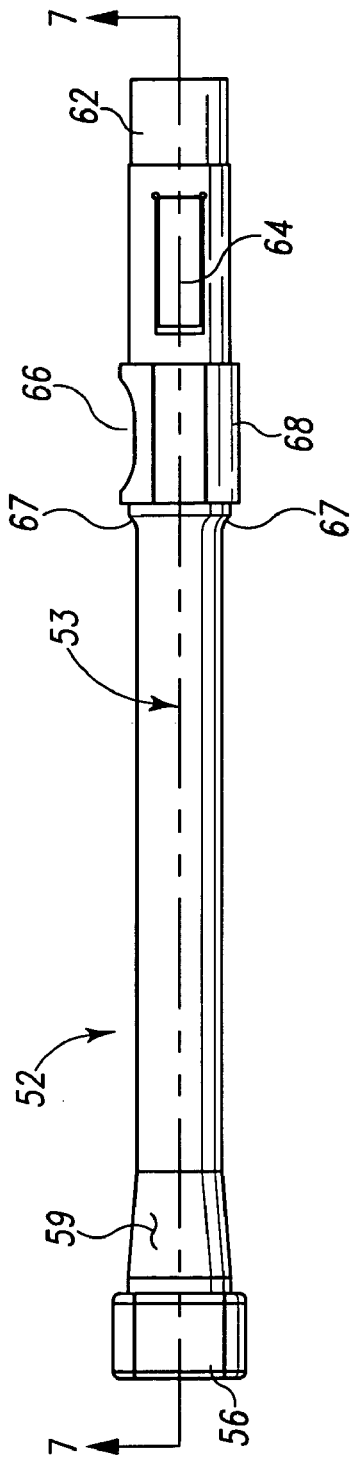
Fig. 4
Fig. 5

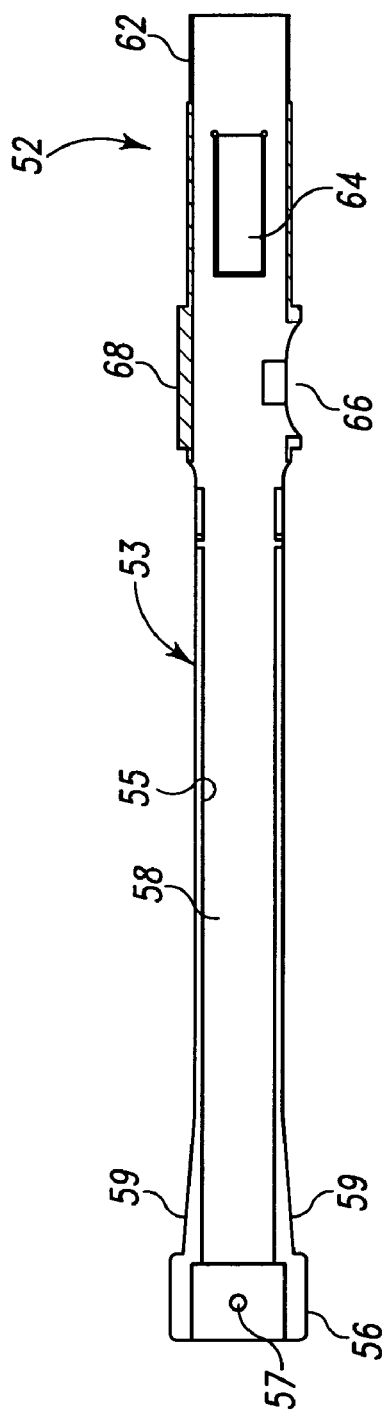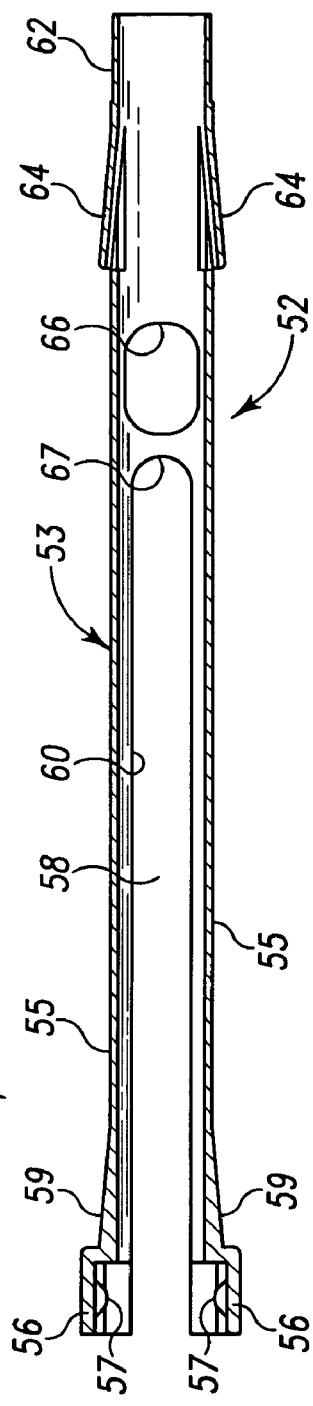
Fig. 6
Fig. 7

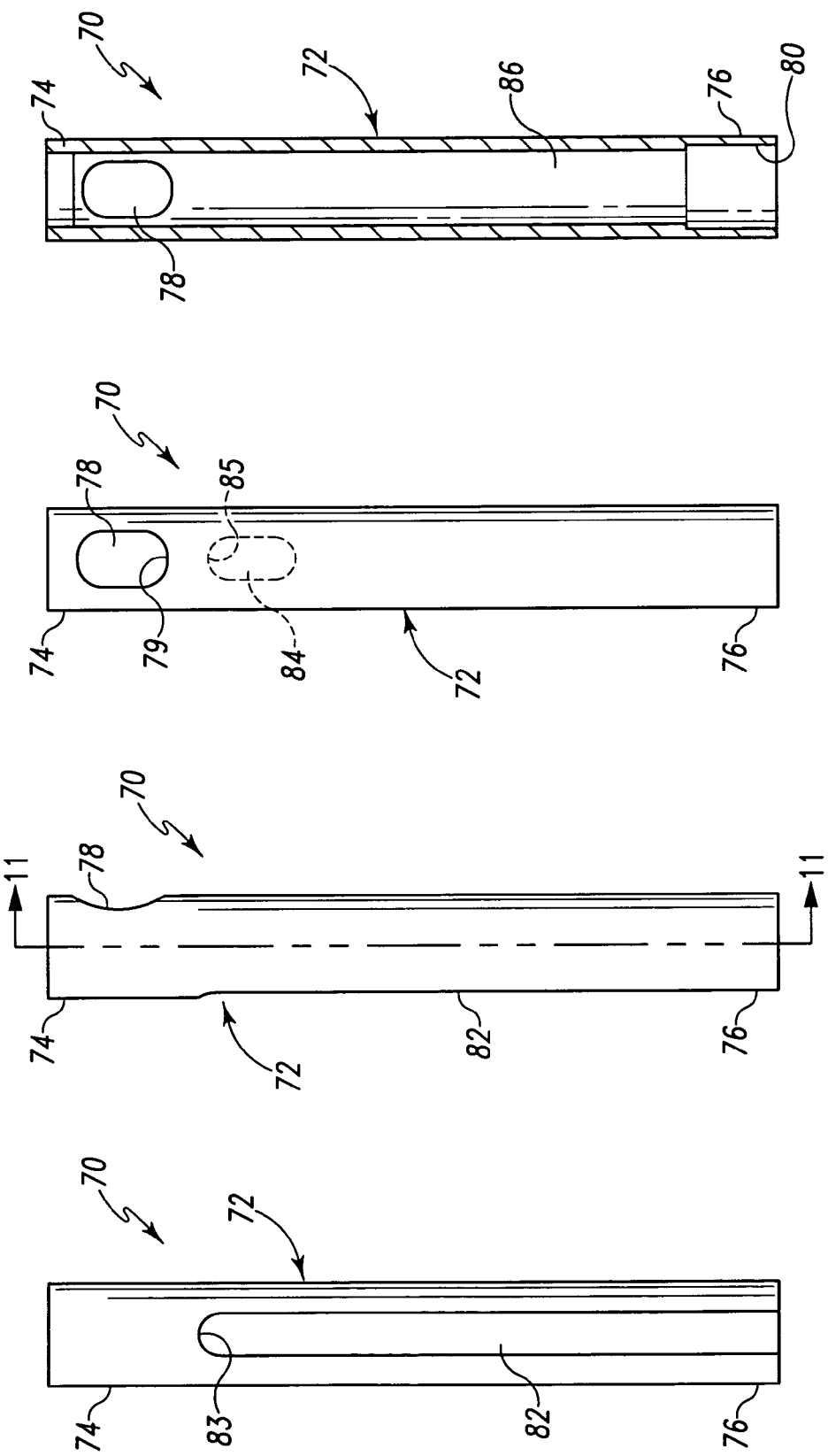

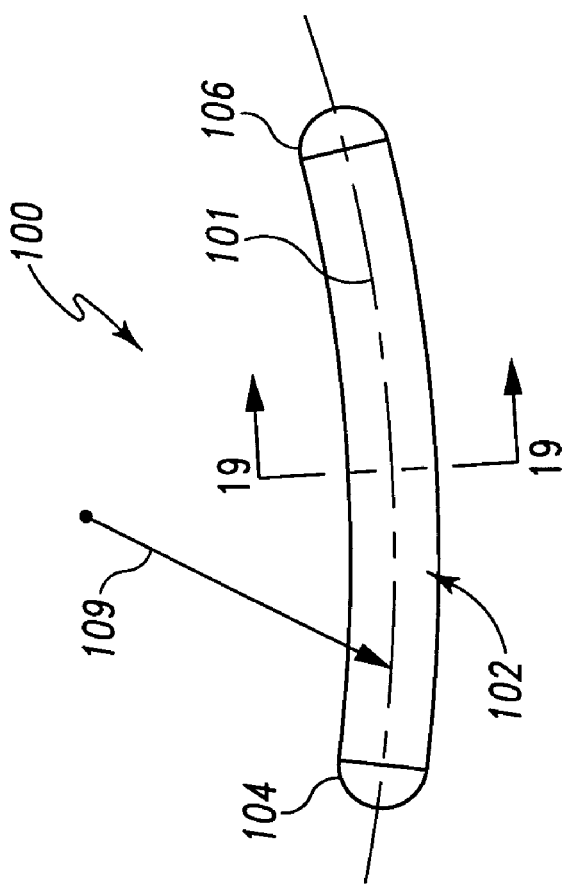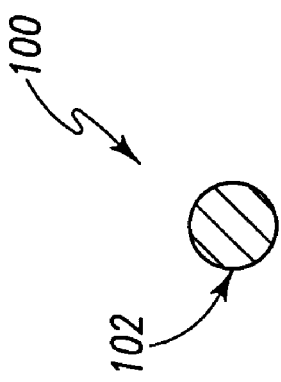
Fig. 18
Fig. 19

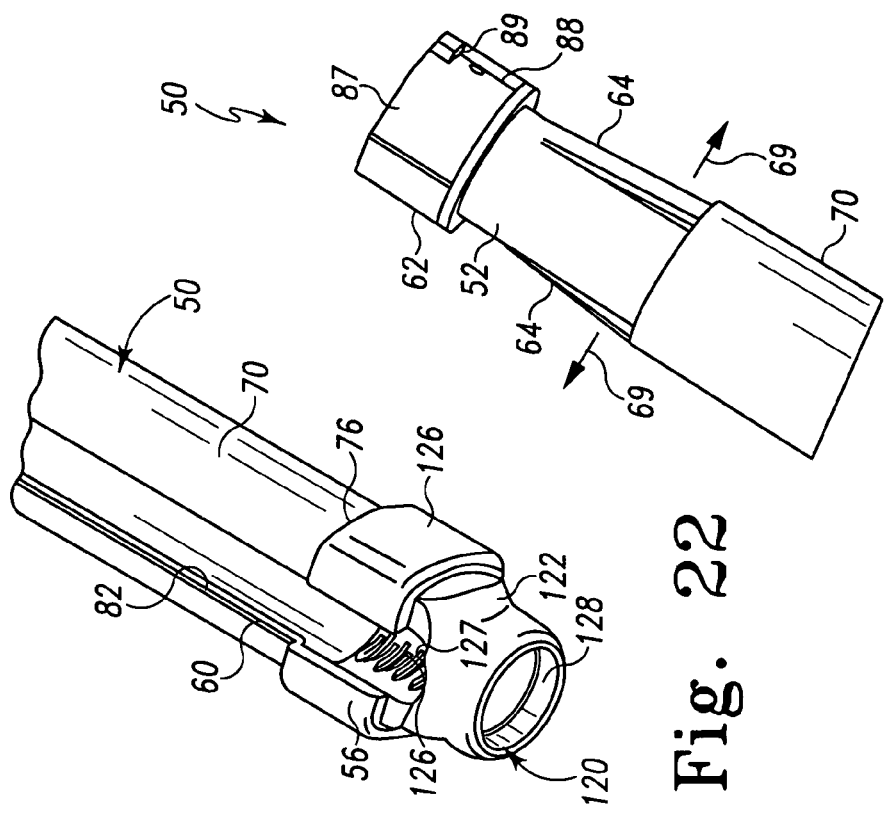
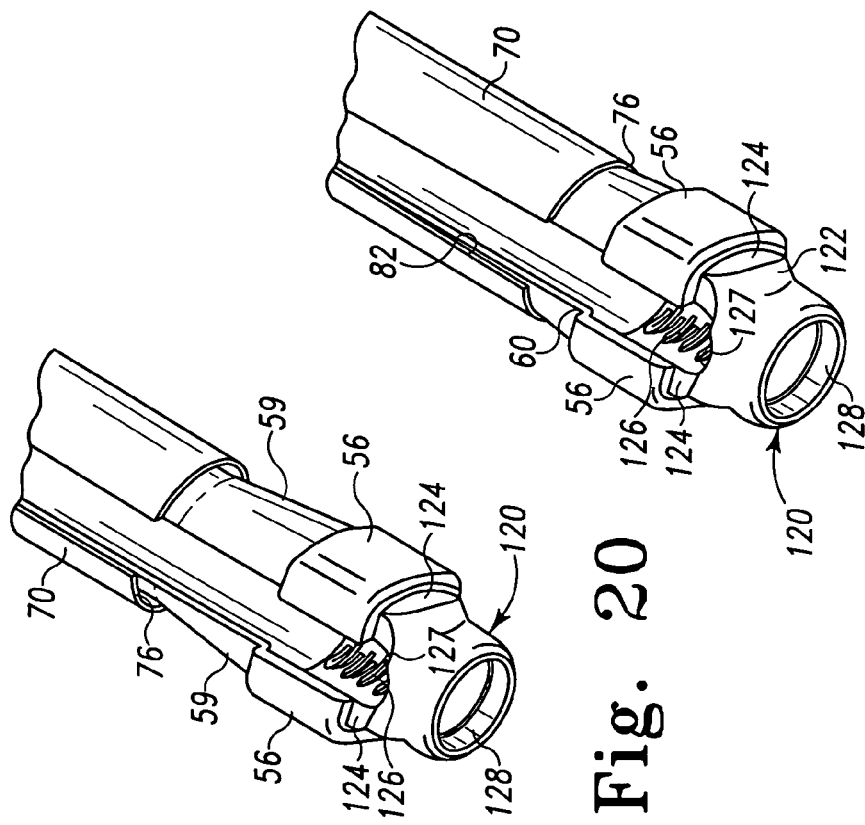
Fig. 20
Fig. 21
Fig. 22
Fig. 23

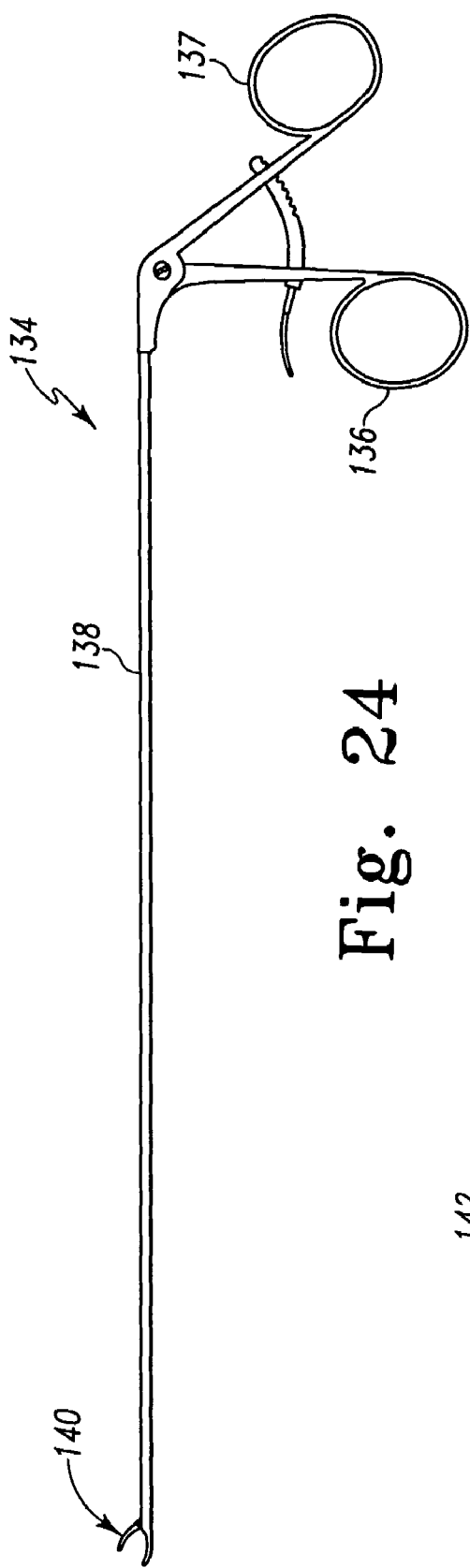
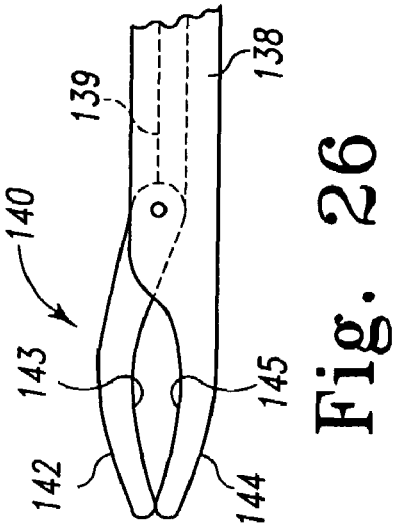
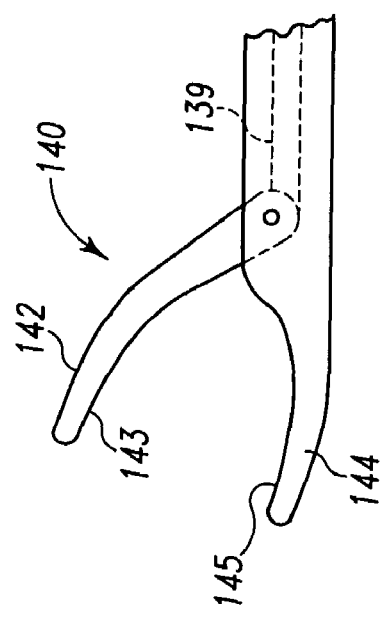
Fig. 24
Fig. 25
Fig. 26

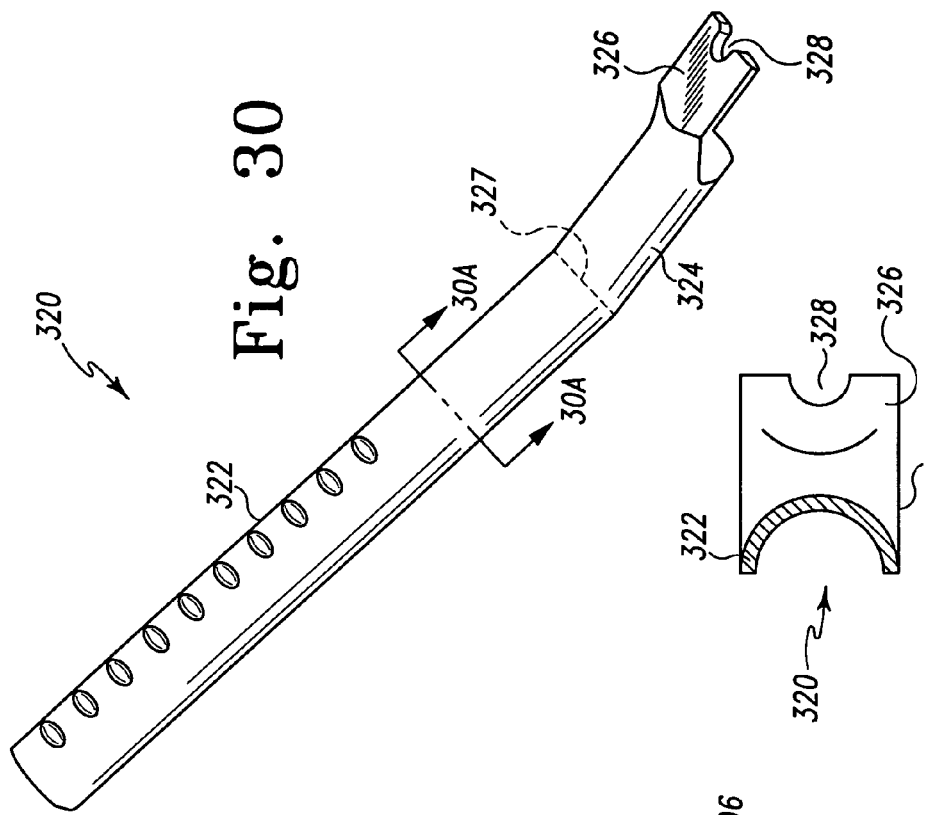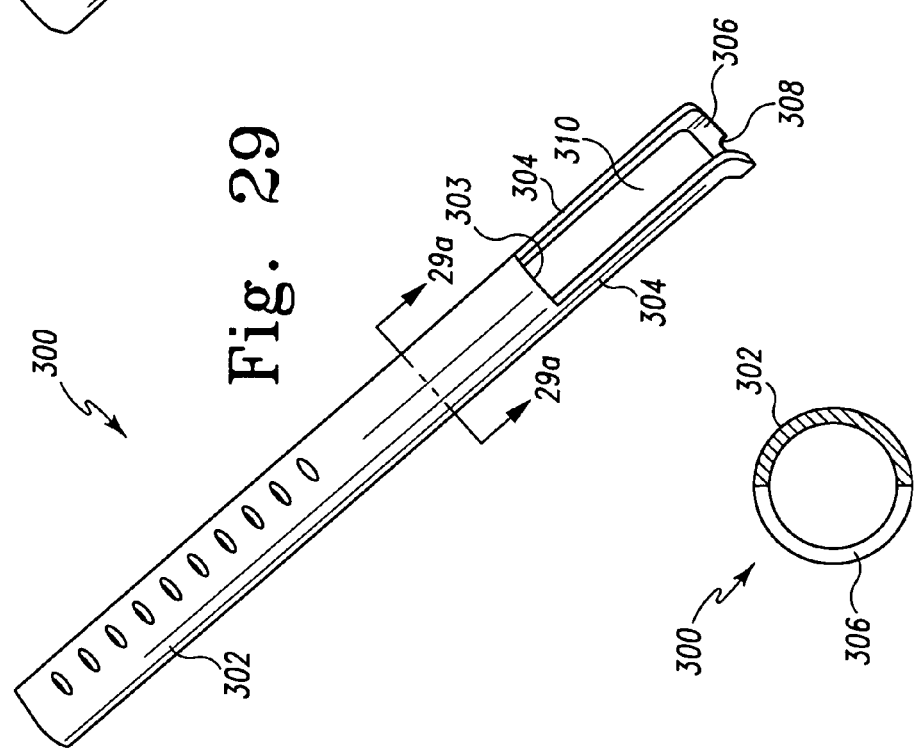

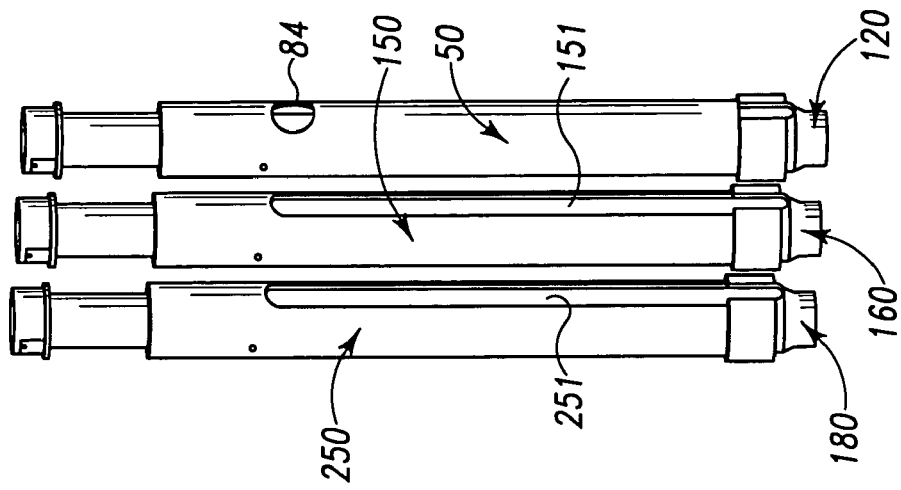
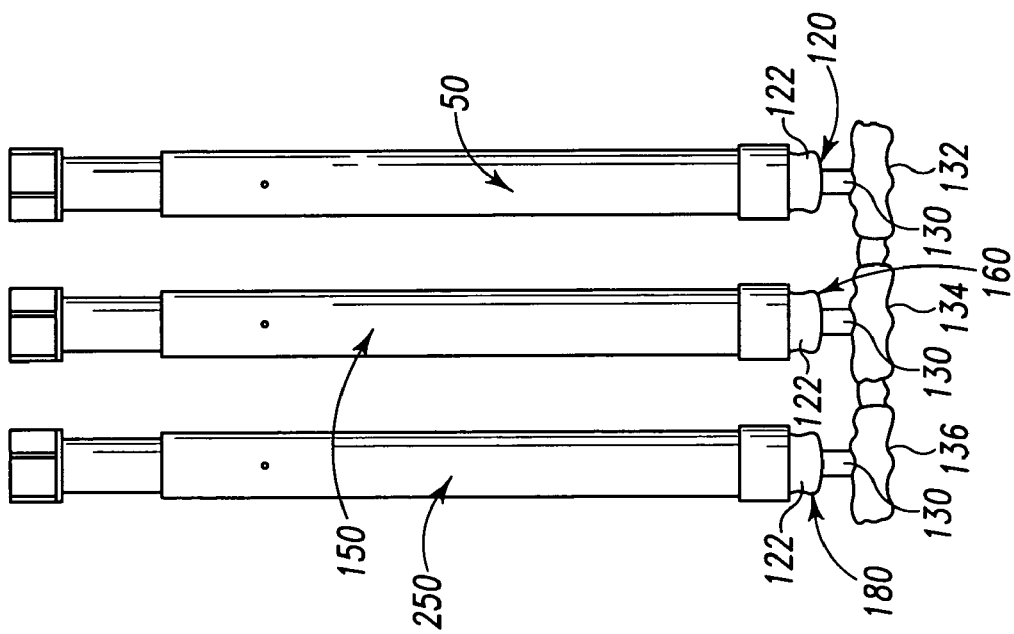

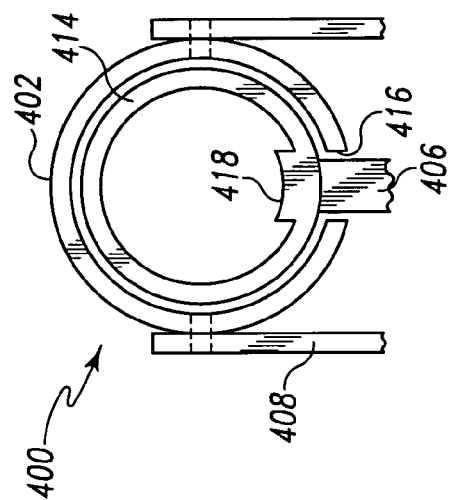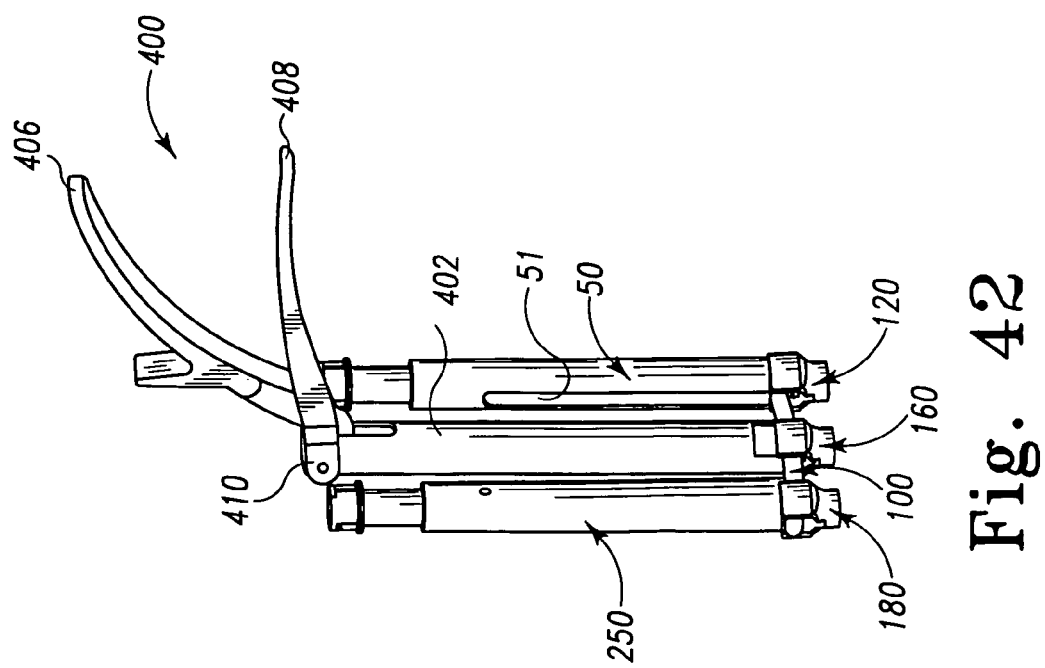

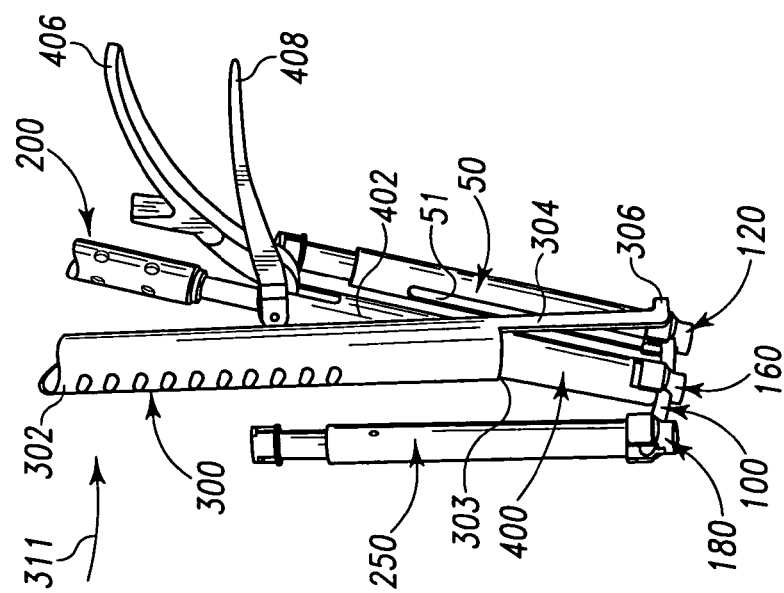

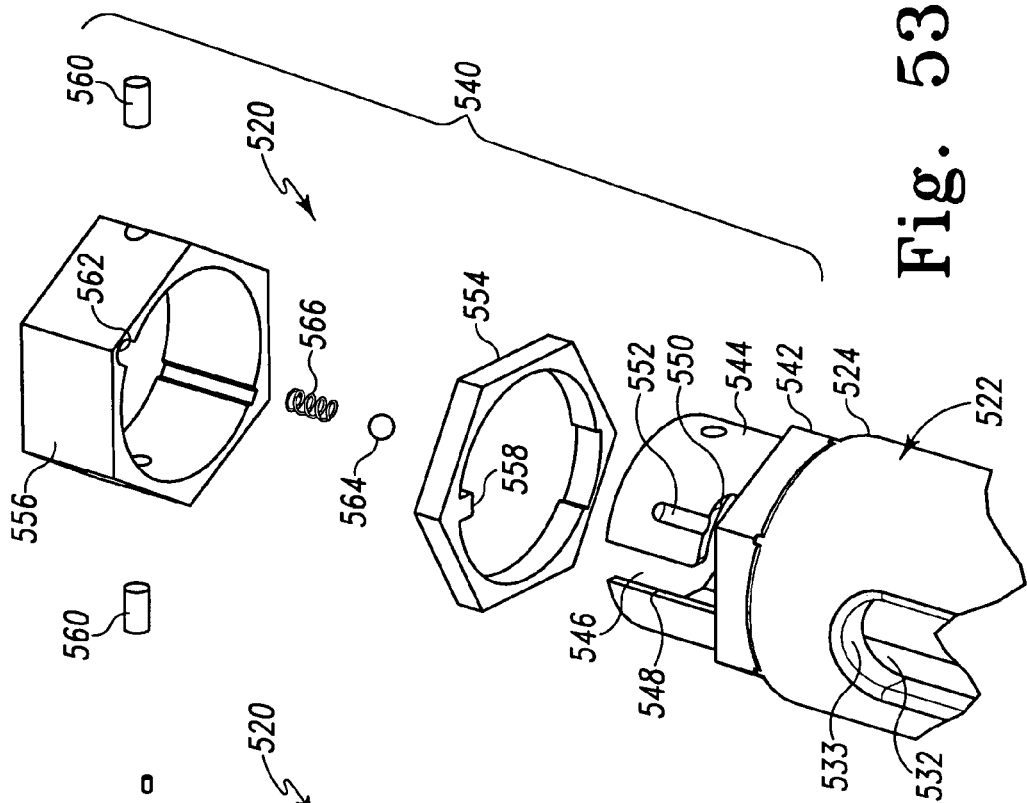
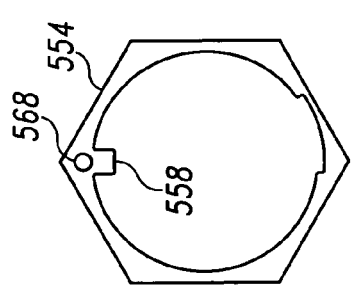
Fig. 53
Fig. 52
Fig. 53A

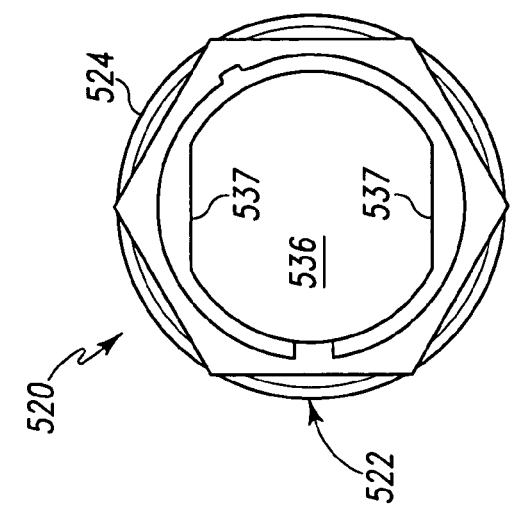
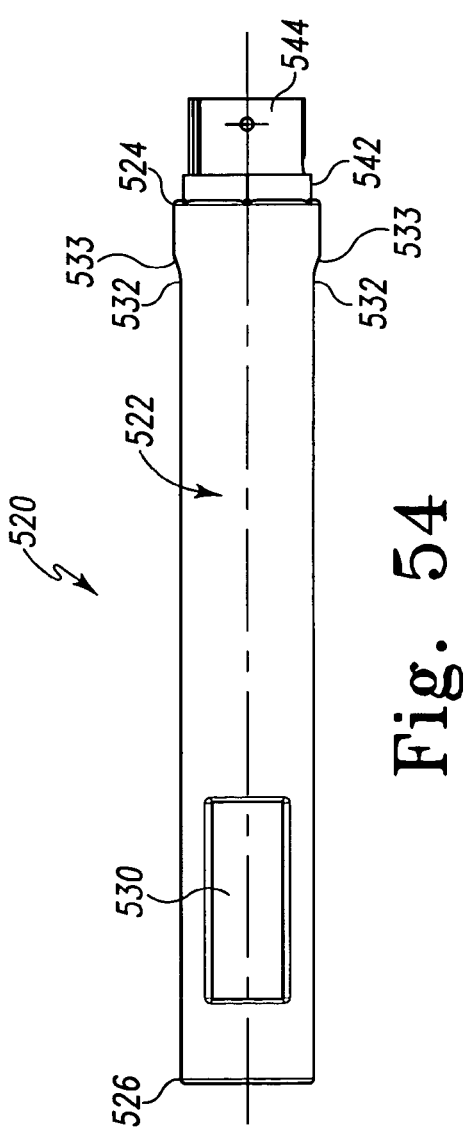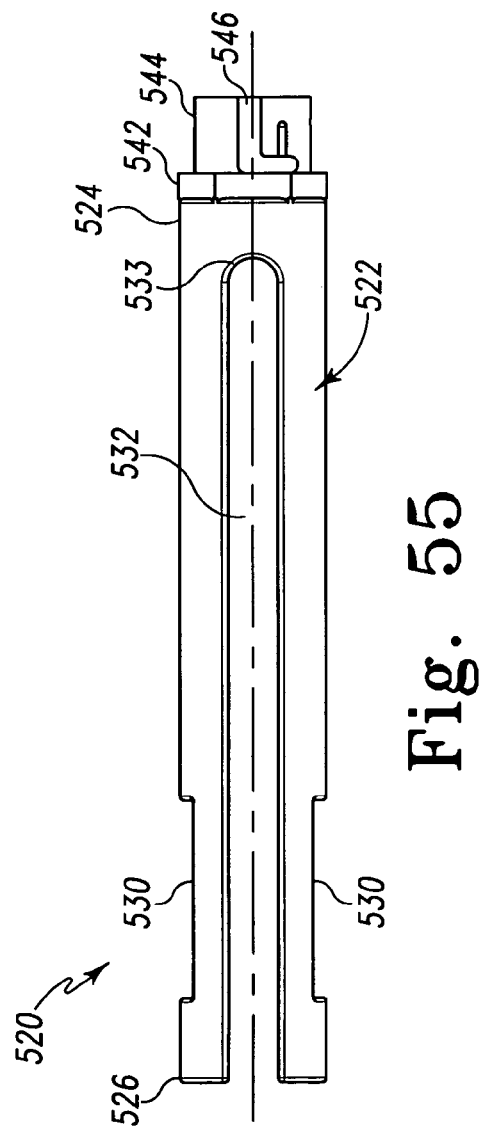

SYSTEM AND METHOD FOR POSITIONING A CONNECTING MEMBER ADJACENT THE SPINAL COLUMN IN MINIMALLY INVASIVE PROCEDURES

BACKGROUND

Orthopedic devices such as spinal rods, plates, tethers, staples and other devices can be secured along the spinal column between one or more vertebral levels to stabilize the one or more vertebral levels. While surgical procedures along the spinal column for placement of such devices are becoming less invasive, the decrease in space available in the approach to the surgical site and at the surgical site for handling and manipulating of the devices increases the difficulty in maneuvering, maintaining and finally positioning of the devices during the procedure. Furthermore, the small and intricate parts commonly associated with such orthopedic devices can increase the difficulty of the installation procedure. Accordingly, systems and devices which facilitate placement of orthopedic devices along the spinal column are desirable.

BRIEF DESCRIPTION OF THE FIGURES

FIG. 4 is an elevation view of an engaging member comprising a portion of a first extender useable with the system of FIG. 1.

FIG. 5 is an elevation view of the engaging member of FIG. 4 rotated 90 degrees about its longitudinal axis.

FIG. 6 is a section view through line 6-6 of FIG. 4.

FIG. 7 is a section view through line 7-7 of FIG. 5.

FIG. 8 is an elevation view of an actuator useable with the engaging member of FIG. 4 to form a first extender useable with the system of FIG. 1.

FIG. 9 is an elevation view of the actuator of FIG. 8 rotated 90 degrees about its longitudinal axis.

FIG. 10 is an elevation view of the actuator of FIG. 8 rotated 180 degrees about its longitudinal axis.

FIG. 11 is a section view through line 11-11 of FIG. 9.

FIG. 18 is an elevation view of one embodiment connecting member positionable adjacent the spinal column with the system of FIG. 1.

FIG. 19 is a section view along line 19-19 of FIG. 18.

FIG. 20 is a perspective view showing the distal portion of an extender before final engagement with an anchor.

FIG. 21 is a perspective view showing the distal portion of the extender of FIG. 21 advanced toward final engagement with the anchor.

FIG. 22 is a perspective view showing the distal portion of the extender of FIG. 21 in final engagement with the anchor.

FIG. 23 is a perspective view showing the proximal portion of the extender of FIG. 22.

FIG. 24 is an elevation view of a rod holder useable with the system of FIG. 1.

FIG. 25 is an elevation view of a distal portion of the rod holder in an open position.

FIG. 26 is an elevation view of a distal portion of the rod holder in a closed position.

FIG. 29 is a perspective view of a compressor useable with the system of FIG. 1 to deliver a compressive force between anchors engaged to the spinal column.

FIG. 29A is a section view through line 29A-29A of FIG. 29.

FIG. 30 is a perspective view of a distractor useable with the system of FIG. 1 to deliver a distractive force between anchors engaged to the spinal column.

FIG. 30A is a section view through line 30A-30A of FIG. 30.

FIG. 32 shows three extenders mounted to anchors engaged to the spinal column.

FIG. 33 is another view of the three extenders and anchors of FIG. 32.

FIG. 42 shows the reduction instrument locked to the second extender and manipulated to finally reduce the connecting member into the anchors.

FIG. 42A shows a top plan view of the reduction instrument engaged to the second extender.

FIG. 43 shows the distal portions of the locked reduction instrument and extenders with the connecting member finally reduced into the anchors.

FIG. 44 shows the compressor of FIG. 29 positioned around the first and second extenders and engaged to the first anchor to deliver a compressive force between the first and second anchors.

FIG. 45 shows the reduction instrument on the first extender and the plug driver of FIG. 28 positioned through the first extender to secure the finally reduced connecting member to the first anchor.

FIG. 52. is an exploded perspective view of an actuator comprising a portion of the extender of FIG. 49.

FIG. 53 is an enlarged detail view of a proximal portion of the actuator of FIG. 52.

FIG. 53A is a top plan view of a locking ring comprising a portion of the actuator of FIG. 52.

FIG. 54 is an elevation view of the actuator of FIG. 52.

FIG. 55 is an elevation view of the actuator of FIG. 52 rotated 90 degrees about its longitudinal axis from its FIG. 54 orientation.

FIG. 56 is proximal end view of the actuator of FIG. 52.

DESCRIPTION OF THE ILLUSTRATED EMBODIMENTS

Figure 3:
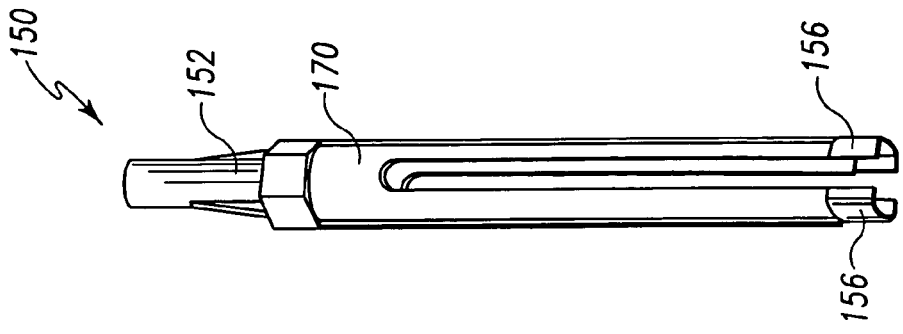
FIG. 3 is a perspective view of a second extender of the system of FIG. 1.

For the purposes of promoting an understanding of the principles of the invention, reference will now be made to the embodiments illustrated in the drawings and specific language will be used to describe the same. It will nevertheless be understood that no limitation of the scope of the invention is thereby intended. Any such alterations and further modifications in the illustrated devices and described methods, and any such further applications of the principles of the invention as illustrated herein are contemplated as would normally occur to one skilled in the art to which the invention relates.

Figure 1:
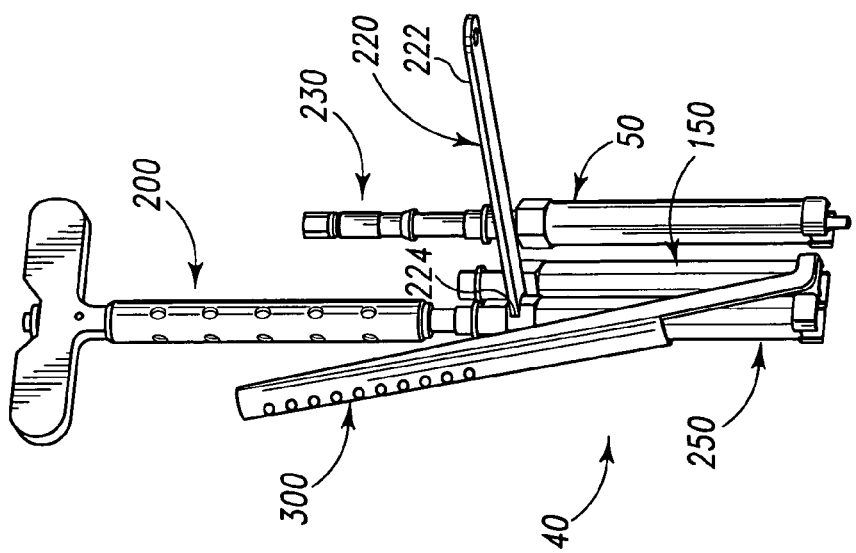
FIG. 1 is a perspective view of a system for positioning a connecting member along the spinal column in a minimally invasive procedure.

Referring to FIG. 1 there is shown a system 40 for positioning a connecting member adjacent the spinal column in a minimally invasive surgical procedure. Although system 40 is particularly suited for minimally invasive surgical procedures, it is not restricted to such. Furthermore, although its use and application is described with regard to spinal surgery, applications in surgeries other than spinal surgery are also contemplated. In one form, system 40 provides at least a pair of extenders mountable to anchors engaged to the spinal column. The extenders extend proximally from the anchors, and guide the placement of a connecting member from a position remote from the spinal column to a position adjacent the spinal column. The extenders are configured so that when the connecting member is adjacent the spinal column, the connecting member extends between the at least a pair of anchors. The connecting member can be secured to the anchors and provide stabilization of the spinal column segment to which the anchors are attached.

In one embodiment, one of the at least a pair of extenders includes an entry hole and/or slot in the side of the extender to allow side entry of the connecting element into the extender. In another embodiment, the at least a pair of extenders includes three extenders. The outermost extenders each include at least one slot oriented toward the middle extender. The middle extender includes opposite slots through which the connecting element extends and is received in the adjacent slots of the outermost extenders.

In one embodiment, the connecting member is an elongated rod and the anchors are bone screws. The bone screws can be multi-axial type screws with a receiver member pivotally mounted to the proximal end of a screw portion. The connecting member can be received in, on, or about the receiving members and engaged thereto. The connecting member can be rigid, semi-rigid, flexible, elastic, non-compression load bearing, or other suitable form for extending between and stabilizing adjacent portions of the spinal column when secured thereto.

In FIG. 1, system 40 includes a first extender 50, a second extender 150 and a third extender 250. Extenders 50, 150, and 250 are engageable to respective ones of a first anchor 120, a second anchor 160 and a third anchor 180 engaged to respective ones of adjacent vertebrae, as shown in FIG. 32. It should be understood, however, that the system and techniques discussed herein may employ only two extenders and two anchors, or three or more extenders and anchors. Extenders 50, 150, 250 extend proximally from the respective anchors through the tissue along the spinal column such that their proximal ends project from the skin and tissue of the patient for access by the surgeon. Extenders 50, 150, 250 define a minimally invasive path for delivery of the connecting member through the tissue of the patient to the anchors engaged to the vertebrae. The minimally invasive path reduces and/or minimizes the tissue retraction and dissection required to accommodate delivery of the connecting member to the surgical space along the spinal column.

System 40 may employ various instruments to facilitate selection of the connecting member, placement of the connecting member through the extenders and to the anchors, securement of the connecting member to the anchors, and manipulation of the vertebra and/or anchors to a desired position or condition. For example, FIG. 1 shows an anchor driver 230 positionable through any one of the extenders, such as extender 50 as shown, to engage the anchor to the vertebra. FIG. 1 also shows a plug driver 200 positionable through any one of the extenders, such as extender 250 as shown, to attach a plug to the anchor to secure the connecting member to the anchor. A counter-torque device 220, such as a wrench or handle arm, can be secured to any one of the extenders, such as extender 250 as shown, to hold the anchor attached to the extender in position as torque is applied to seat the plug relative to the anchor. A compressor 300 is positionable relative to at least one of the extenders to facilitate application of a compressive force between anchors, allowing compression between vertebrae to be applied prior to final attachment of the connecting member to each anchor.

Other instruments not shown in FIG. 1 are also contemplated with system 40. For example, a distractor 320 shown in FIG. 30 facilitates application of a distraction force to anchors to distract vertebrae of the spinal column segment prior to final attachment of the connecting member to each anchor.

Figure 31:
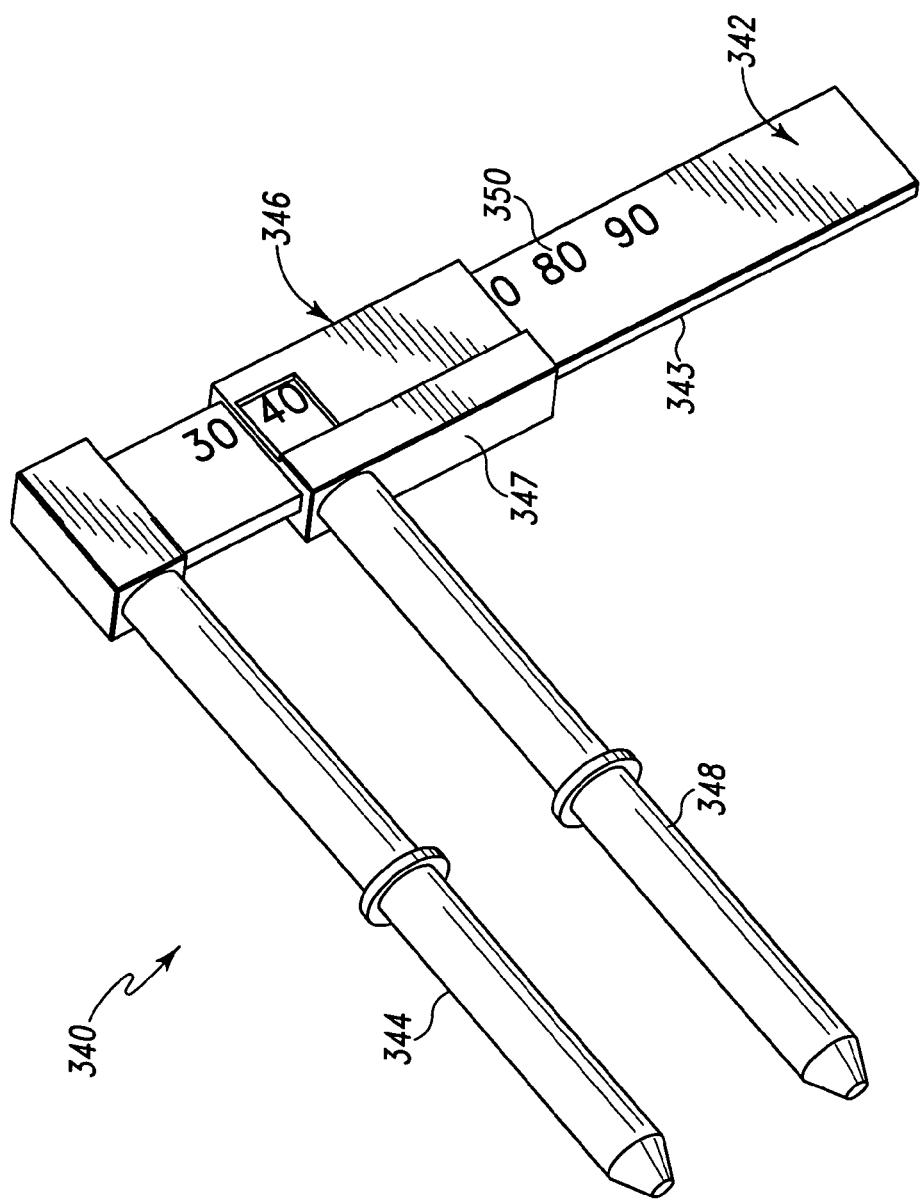
FIG. 31 is a perspective view of calipers useable with the system of FIG. 1 to measure the distance between extenders to determine the size of a connecting member for positioning adjacent the spinal column using the system of FIG. 1.
Figure 40:
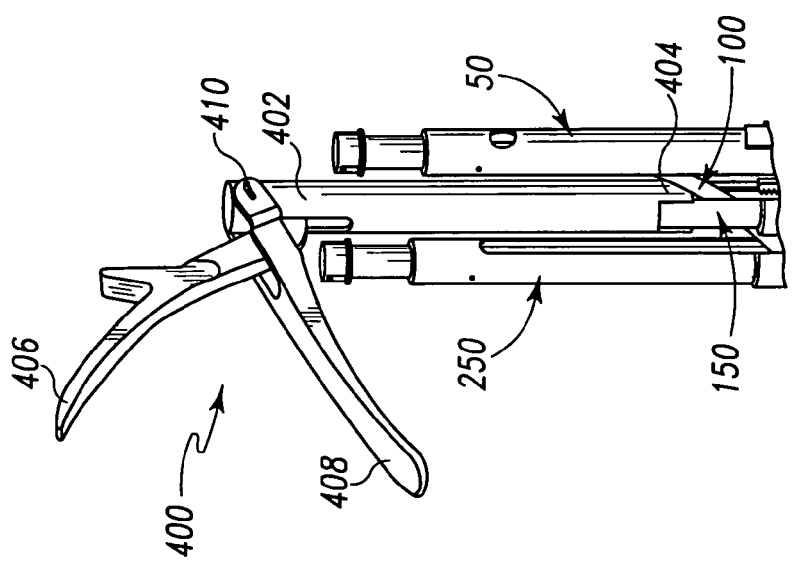
FIG. 40 shows the extenders of FIG. 32 with the connecting member positioned therethrough and a reduction instrument positioned over the second extender.

Calipers 340 shown in FIG. 31 allow a distance between the outermost extenders to be measured for sizing of the length of the connecting member to be positioned between the anchors. A holding instrument 134 shown in FIG. 24 is adapted to grasp and hold the connecting member placed between the extenders, and can be employed to move the connecting member distally along the extenders toward and into the anchors. A reduction instrument 400 shown in FIG. 40 is positionable along any one of the extenders and engageable thereto to provide a mechanical advantage for reduction of the connecting member into one or more of the anchors. The reduction instrument 400 may further be employed as a counter torque instrument.

Examples of suitable connecting members that extend between the anchors include rods, wires, tethers, strands, cables, bands, plates, and struts. The connecting member may include one component, or may include two or more components. One embodiment connecting member is shown in FIG. 18, and includes connecting member 100 having an elongated rod-shaped body 102. Body 102 extends along a longitudinal axis 101 between a first end 104 and an opposite second end 106. Body 102 is curved about a radius 109 formed by longitudinal axis 101. Ends 104, 106 include generally the same size and shape, although such is not required. Other embodiments contemplate that body 102 is linear, a combination of linear and curved segments, a combination of linear segments angled relative to one another, or a combination of segments having differing curvatures. Body 102 has a uniform cross-section along its length, which can be circular as shown in FIG. 19. However, non-uniform cross-sections are also contemplated. In one embodiment, connecting member is an elongated rod made from a metal alloy such as titanium. Other materials are also contemplated, including resorbable materials, non-resorbable material, polymers, elastomers, ceramics, other metals and metal alloys, shape memory materials, bone and bone substitute material, composites, and combinations of materials.

Figure 2:
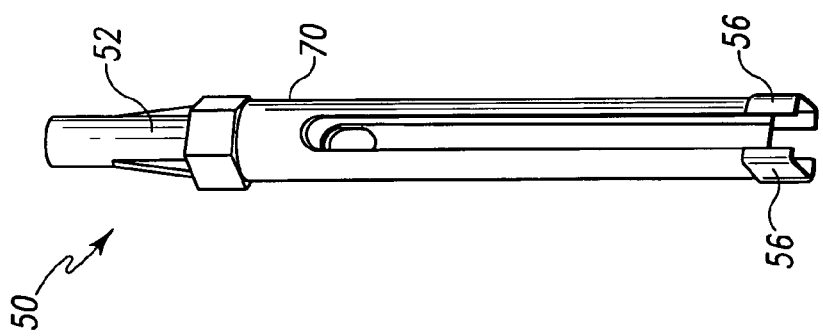
FIG. 2 is a perspective view of a first extender of the system of FIG. 1.

Referring now to FIG. 2, extender 50 will be discussed further. Extender 50 includes an engaging member 52 housed within an actuator 70. Engaging member 52 includes opposing feet 56 moveable toward and away from one another in response to a position of actuator 70 relative thereto. As shown in FIGS. 4-7, engaging member 52 includes a body 53 extending between distal feet 56 and a proximal collar 62. Body 53 defines a passage 58 extending between and opening at the distal and proximal ends of body 53. Feet 56 each include a projection 57 extending into passage 58 for engagement with corresponding indentations formed in the opposite sides of a receiver member of an anchor, discussed further below. The interface between projections 57 and the receiver member resists axial displacement of the receiver member relative to the engaging member 52 when engaged thereto.

Engaging member 52 further includes elongated slots 60 formed on opposite sides thereof which open passage 58 to the exterior of body 53 along a major portion of the length of body 53. Slots 60 have sufficient length so that the proximal terminal ends 67 of slots 60 can be accessed for delivery of the connecting member through the slots 60. Slots 60 extend from between feet 56 proximally to a location adjacent an intermediate portion 68 of body 53. Opposing legs 55 extend proximally from feet 56 and along slots 60. Camming surfaces 59 extend along the outer surface of respective ones of the legs 55 from a maximum height adjacent the respective foot 56, and taper proximally along a portion of the length of the respective leg 55.

Figure 38:
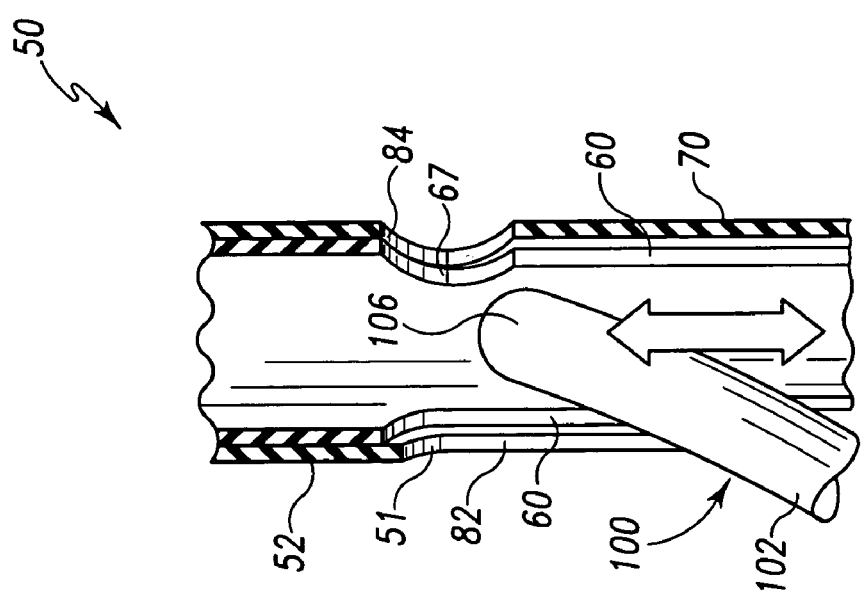
FIG. 38 is a detailed view of a portion of the first extender in section showing the connecting member in the first extender.

In the illustrated embodiment, an entry hole 66 is formed through intermediate portion 68 on one side of body 53 adjacent one of the slots 60. Entry hole 66 is spaced proximally of the proximal terminal end 67 of the adjacent slot 60. The opposing side of intermediate portion 53 does not include an entry hole 66, although the provision of the same is not precluded. As discussed further below, the connecting member is received through the entry hole for delivery between the extenders 50, 150, 250. It is further contemplated that the connecting member can be delivered through an elongated slot rather than an entry hole. In another embodiment, no entry hole 66 is provided in body 53. Rather, the proximal terminal end 67 of one of the slots 60 is sized to accommodate passage of the connecting member therethrough, as shown in FIG. 38.

Engaging member 52 further includes tabs 64 projecting outwardly therefrom proximally adjacent intermediate portion 68. Tabs 64 are coupled at their proximal ends to body 53 with an integral living hinge, and are biased so that their distal ends normally project outwardly from body 53. The distal ends of tabs 64 are moveable toward one another about their proximal end hinges to facilitate placement of actuator 70 over engaging member 52 and to engage the proximal end of actuator 70 and secure it to engaging member 52. Other embodiments contemplate other locking arrangements between the engaging member and actuator, including slide locks, spring-actuated buttons, bayonet locks, interference fits, fasteners, and ball-detent mechanisms, for example.

Actuator 70 is further shown in FIGS. 8-11. Actuator 70 includes a body 72 extending between a distal end 76 and a proximal end 74. A bore 86 extends between and opens at distal and proximal ends 76, 74. Bore 86 includes an enlarged portion 80 adjacent distal end 76. Actuator 70 further includes an elongate slot 82 extending along one side thereof from distal end 76 to a proximal terminal end 83 spaced distally of proximal end 74. The side of body 72 opposite slot 82 includes an entry hole 78 in communication with bore 86. In the illustrated embodiment, entry hole 78 is spaced proximally of the proximal terminal end of slot 82, and includes a distal terminal end 79 that is aligned with the proximal terminal end 83 of slot 82. In an alternate embodiment, actuator 70 provided with an entry hole 84 (indicated in dashed lines in FIG. 10) that includes a proximal terminal end 85 located in alignment with the proximal terminal end 83 of slot 82. In still other embodiments, the proximal and/or distal terminal ends of the entry hole are not aligned with the slot.

When extender 50 is assembled, engaging member 52 is positioned in bore 86 of actuator 70, and actuator 70 is movable distally and proximally along engaging member 52, as shown in FIGS. 20-22, to selectively engage and release an anchor positioned therebetween, such as anchor 120. As actuator 70 is advanced distally along engaging member 52, as shown in FIGS. 20-21, the distal ends of tabs 64 move inwardly toward one another to allow passage of actuator 70 thereover. The enlarged bore portion 80 of actuator 70 receives camming surfaces 59 and act on the camming surfaces 59 to move feet 56 toward one another. The portion of bore 86 extending proximally from enlarged portion 80 provides a close fit with intermediate portion 68 of body 53 of engaging member 52, reducing or eliminating play between actuator 70 and engaging member 52 when assembled. In the illustrated embodiment, intermediate portion 68 projects about body 53, and includes a non-circular shape in cross-section.

When actuator 70 is displaced completely distally relative to engaging member 52, as shown in FIG. 2 and in FIGS. 22-23, distal end 76 of actuator 70 is positioned adjacent the proximally facing shoulder of the adjacent feet 56. The inner surface of actuator 70 defining enlarged portion 80 of bore 86 contacts the camming surfaces 59 to force feet 56 toward one another to clamp a receiver member 122 of anchor 120 therebetween. When actuator 70 is finally positioned, tabs 64 return to their pre-insertion configuration, as indicated by arrows 69 in FIG. 23, and extend outwardly so that their distal ends engage the proximal end 74 of actuator 70. Tabs 64 maintain actuator 70 in position relative to engaging member 52 to ensure that the anchor remains clamped thereto between feet 56.

In its assembled and clamping position, extender 50 provides an avenue for insertion of a connecting member therethrough for positioning between extenders 50, 150, 250. For example, if an entry hole 66 is provided in engaging member 52, entry hole 66 is aligned with entry hole 78 of actuator 70. As discussed further below, a connecting member can be positioned through the aligned entry holes 66, 78. Entry holes 66, 78 can be oval in shape to facilitate placement of the connecting member at a steep angle therethrough, as discussed below with respect to FIG. 39. Circular entry holes and other elongated shapes for the entry holes are also contemplated. Furthermore, in the assembled and clamping position, the proximal terminal end 67 of the slot 60 of engaging member 52 opposite entry hole 66 aligns with proximal terminal end 83 of the slot 82 of actuator 70 adjacent thereto. This allows placement of the connecting member through the aligned slots and into the next adjacent extender 150. The connecting member can be angled to displace its leading insertion end distally relative to its proximal trailing end as it is delivered through the aligned entry holes 66, 78. This positions the leading insertion end of the connecting member distally of the proximal terminal ends 67, 83 of the aligned slots 60, 82 opposite the aligned entry holes 66, 78. The side of actuator 70 opposite slot 82 provides a wall that closes the adjacent slot 60 engaging member 52, preventing the connecting member from passing outside of extender 50 in a direction opposite extender 150.

In an another embodiment, as discussed above, engaging member 52 does not include an entry hole 66. Rather, actuator 70 is provided with an alternate entry hole 84 located in a position aligned with the terminal end 67 of the adjacent slot 60 of engaging member 52. In this embodiment, the connecting member can be positioned through entry hole 84 and the adjacent slot 60 along a path that is generally parallel to its ultimate alignment along the spinal column. It is also contemplated that the connecting member can be inserted at a steep angle, as discussed below with respect to FIG. 39.

Second extender 150 is shown in FIG. 3. Second extender 150 includes an engaging member 152 positioned within a bore of actuator 170. Second extender 150 can be provided with an engaging member 152 that is substantially identical to engaging member 52 of extender 50, and includes feet 156 engageable to an anchor at a distal end thereof. Although an entry hole 66 could be provided with the engaging member 152 of extender 150, engaging member 152 can be provided without an entry hole 66 since the connecting member is received into the aligned slots of engaging member 152 and actuator 170 of second extender 150 from the aligned slots 82, 60 of first extender 50.

Figure 14:
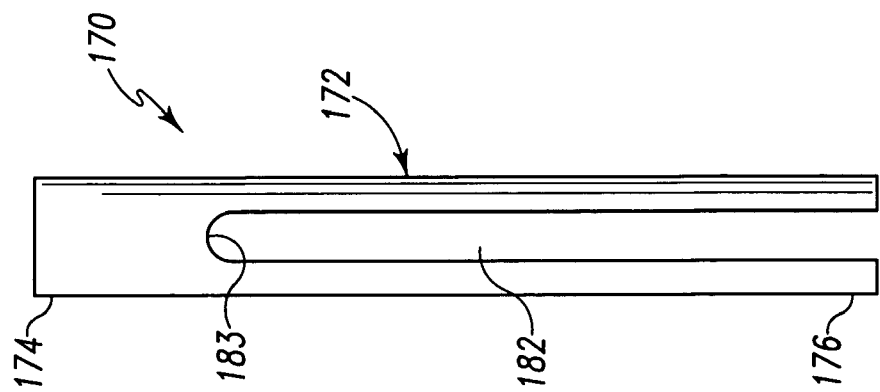
FIG. 14 is an elevation view of the actuator of FIG. 12 rotated 180 degrees about its longitudinal axis.
Figure 13:
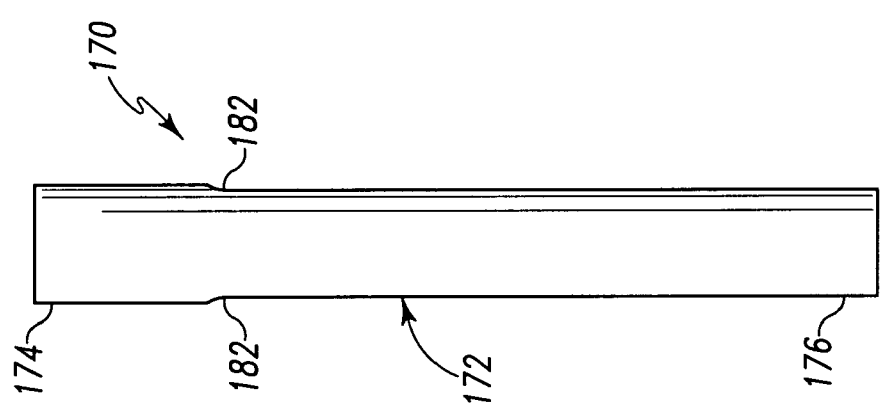
FIG. 13 is an elevation view of the actuator of FIG. 12 rotated 90 degrees about its longitudinal axis.
Figure 12:
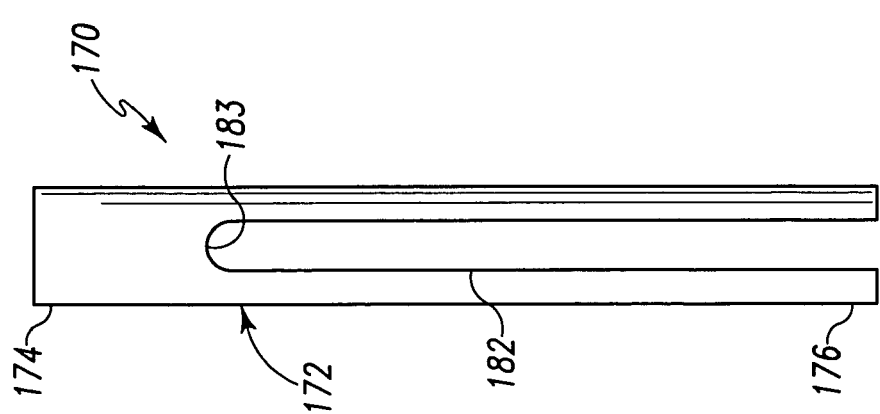
FIG. 12 is an elevation view of an actuator useable with an engaging member to comprise a portion of a second extender useable with the system of FIG. 1.

As shown in FIGS. 12-14, actuator 170 of second extender 150 includes a body 172 extending between a distal end 176 and a proximal end 174. Body 172 is substantially identical to body 72 of actuator 70, but includes a pair of aligned slots 182 opposite one another on body 172. Opposing slots 182 open at distal end 176 and extend proximally to a proximal terminal end 183 spaced distally of proximal end 174. It is contemplated that slots 182 have the same length as one another, and also the same length as the slots of the engaging member 152 received in actuator 170. By providing aligned slots that open on each side of extender 150, the connecting member can be received from the aligned slots 60, 82 of extender 50 and positioned completely through extender 150 for receipt into the next adjacent extender 250.

Figure 17:
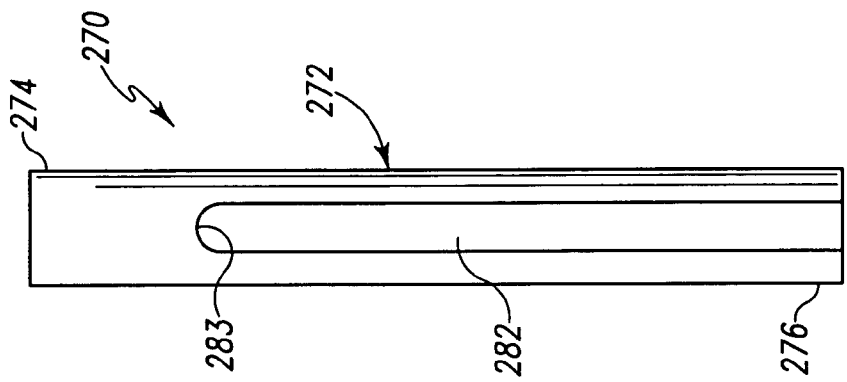
FIG. 17 is an elevation view of the actuator of FIG. 15 rotated 180 degrees about its longitudinal axis.
Figure 16:
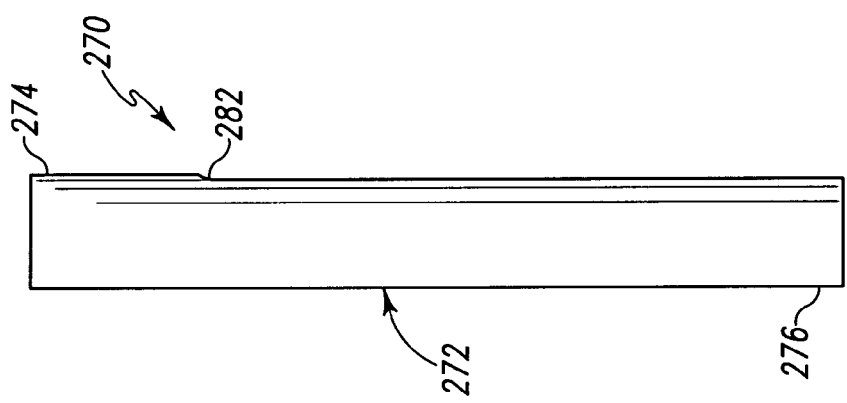
FIG. 16 is an elevation view of the actuator of FIG. 15 rotated 90 degrees about its longitudinal axis.
Figure 15:
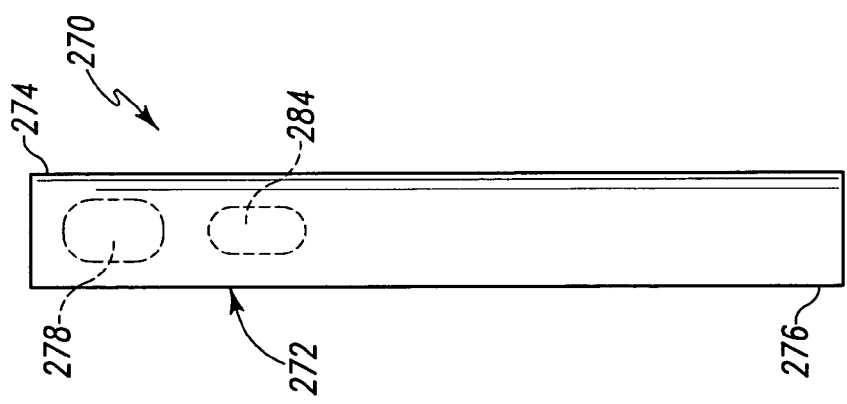
FIG. 15 is an elevation view of an actuator comprising a portion of a third extender useable with the system of FIG. 1.

The third extender 250 can be provided with an engaging member substantially identical to engaging member 152 of second extender 150. Third extender 250 can be provided with an actuator 270 as shown in FIGS. 15-17. Actuator 270 includes a body 272 extending between a distal end 276 and a proximal end 274. Body 272 is substantially identical to body 72 of actuator 70, and includes a single slot 282 along one side thereof, and the opposite side of body 72 is closed by a wall of body 272, similar to actuator 70. Slot 282 opens at distal end 276 and extends proximally to a proximal terminal end 283 spaced distally of proximal end 274. It is contemplated that slot 282 has the same length as and is aligned with one of the slots of the engaging member received in actuator 270. When positioned in its operative orientation, as shown in FIG. 1, the elongated slot of extender 250 is oriented toward and aligned with the slots of extender 150 and extender 50. In still another form, third extender 250 can be provided with an entry hole in one or both of actuator 27 and the engaging member received therein to allow positioning of the connecting member between the extenders from either first extender 50 or third extender 250.

By providing extender 250 with a slot that opens on only one side, the leading insertion end of the connecting member can be positioned into extender 250 but will not extend therefrom in direction opposite first extender 50. The outer closed walls of first extender 50 and third extender 250 thus maintain and constrain the positioning of the connecting member between extenders 50, 150 and 250 during advancement to the anchors attached to the distal ends of the extenders 50, 150, 250.

It is further contemplated, as discussed above, that system 40 can be employed with only a pair of extenders. In such systems extender 50 and extender 250 could be employed since extender 50 and extender 250 are configured to constrain the connecting member between outermost anchors. In systems employing more than three extenders, the two or more middle or intermediate extenders between the first extender 50 and the outermost extender 250 can be identical to second extender 150.

In still another embodiment, it is contemplated that each of the two of more extenders employed in the system can be double slotted like extender 150. In this embodiment, the connecting member is not constrained between the outer extenders, but rather can extend through the slots of each or one of the outer extenders so that the end of the rod is accessible outside the adjacent outer extender. This allows the rod to be grasped or contacted along the outer sides of the extenders for manipulation along the extenders and to the anchors.

Referring to FIGS. 24-26, there is shown a holder for grabbing and manipulating the connecting member positioned between the extenders 50, 150, 250. Holder 134 is configured like a rongeur, and includes proximal first and second handles 136, 137 pivotally coupled to one another. Handles 136, 137 are operatively linked to a grasping mechanism 140 at the distal end of the instrument. An outer shaft 138 is fixed to and extends distally from second handle 137. An inner shaft 139 extends through outer shaft 138 and is pivotally coupled at its proximal end to first handle 136. The distal end of inner shaft 139 is pivotally coupled to a first jaw 142 of grasping mechanism 140. A second jaw 144 extends from outer shaft 138 and is fixed relative thereto. Movement of first handle 136 moves inner shaft 139 proximally, which moves first jaw 142 toward second jaw 144 to effect closing action between jaws 142, 144.

In the illustrated embodiment, grasping mechanism 140 is configured to extend about a connecting member having a circular or rounded cross-section. Jaw 142 includes a concave inner surface 143, and jaw 144 includes a concave inner surface 145. Surfaces 143, 145 are oriented toward one another, and their concavely curved surfaces extend about at least a portion of the perimeter of the connecting member. The grasping mechanism 140 facilitates grasping of the connecting member by holder 134 by providing a clamping or grasping force along a greater length of the outer surface of the connecting member than if the inner surfaces of the jaws were linear. Surfaces 143, 145 can include teeth or roughenings to enhance frictional engagement with the connecting member. Holder 134 includes a low profile so that it can be positioned between adjacent ones of the extenders 50, 150, 250 to grasp the connecting member extending between the extenders 50, 150, 250. Holder 134 can then be moved distally toward the anchors to advance and/or control the connecting member as it is moved toward the anchors.

Holder 134 can be employed in conjunction with one or more plug drivers 200. The one or more plug drivers 200 can be positioned through respective ones of the extenders 50, 150, 250. The plug drivers 200 advance the connecting member along the extenders while holder 134 controls the positioning and orientation of the connecting member between the extenders.

In the illustrated embodiment, holder 134 includes single action type first and second jaws 142, 144. In another embodiment, double action type jaws are contemplated in that each of the jaws 142, 144 pivot when moved between the open and closed positions.

Figure 27:
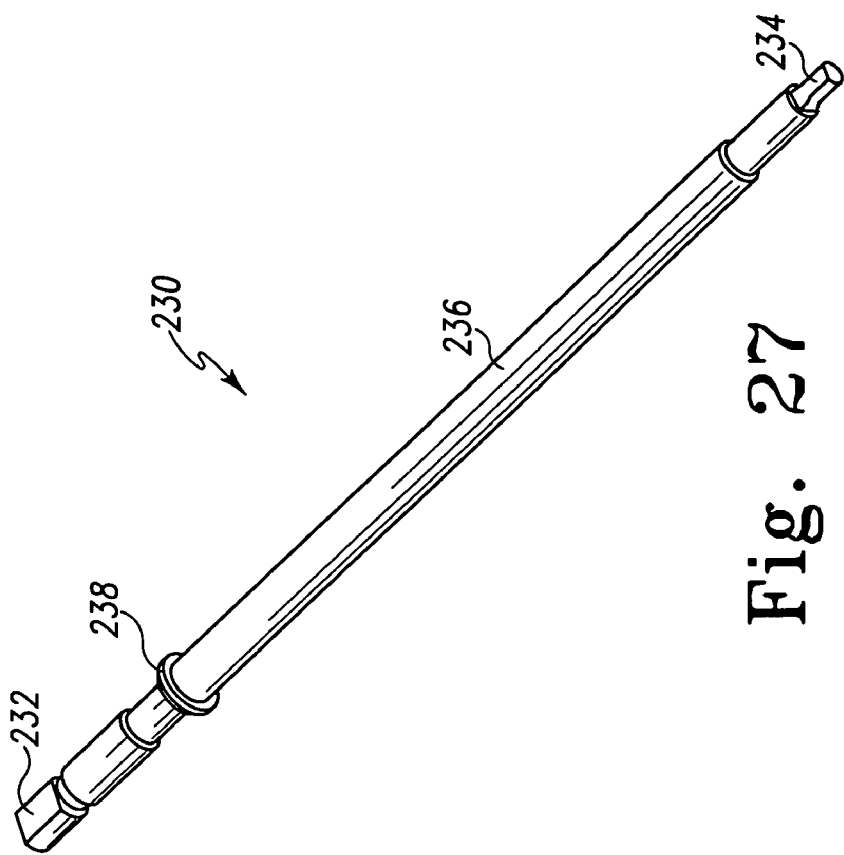
FIG. 27 is a perspective view of an anchor driver useable with the system of FIG. 1 to position an anchor in engagement with the spinal column.

FIG. 27 shows anchor driver 230 in further detail. Anchor driver 230 includes a distal end 234 configured to engage a tool-receiving recess of the anchor, and a shaft 236 extending distally from distal end 234. Shaft 236 includes a proximal connecting portion 232, which can include a cross-section to engage a removable handle, such as a T-handle. In the illustrated embodiment, the non-circular cross-section of connecting portion 232 allows the removable handle to be non-rotatably fitted thereon. Other embodiments contemplate an integral handle for anchor driver 230, and other suitable configurations for proximal connecting portion 232 for removably engaging a handle. A collar 238 is provided about that extends radially shaft 236 adjacent proximal portion 232. Collar 238 provides bulk about shaft 236 to prevent over insertion of anchor drive 230 into an extender. The elongated shaft 236 is sized for positioning through passage of the respective extender to which the anchor is engaged so that the anchor can be engaged to the spinal column with the extender engaged thereto.

Figure 28:
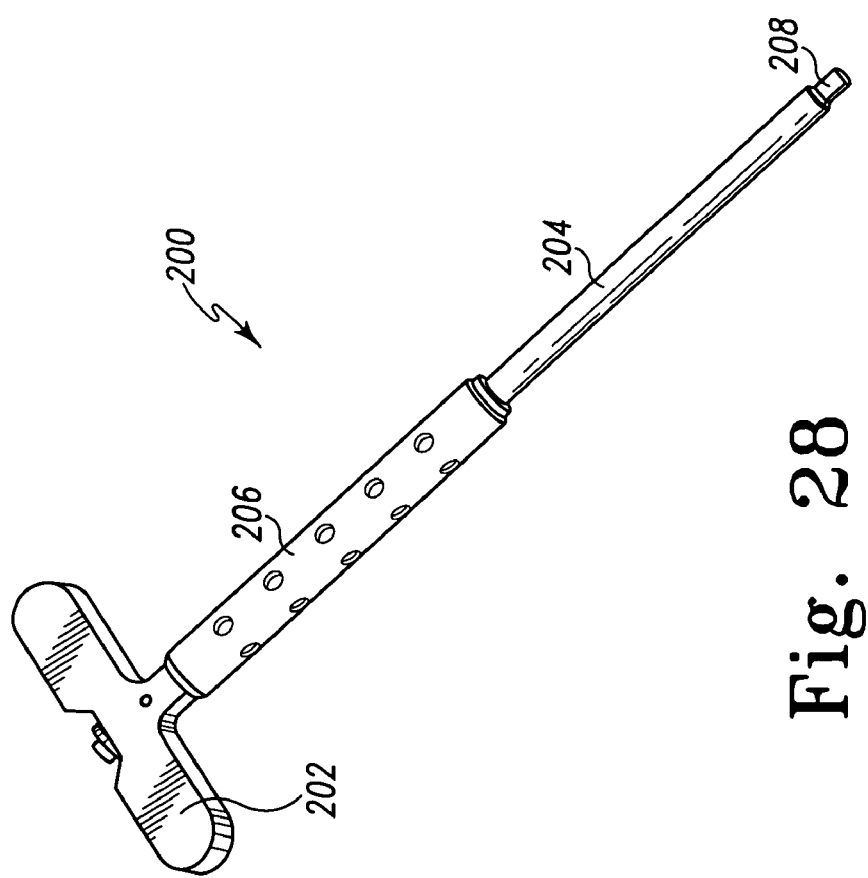
FIG. 28 is a perspective view of a plug driver useable with the system of FIG. 1 to position a plug in engagement with an anchor engaged to the spinal column.

FIG. 28 shows plug driver 200 in further detail. Plug driver 200 includes a distal end 208 configured to engage and removably capture a plug thereon. The plug can be configured to engage the anchor to secure the connecting member in, on or about the anchor. In one embodiment, the plug is a set screw with a proximally opening tool engaging recess. In a further embodiment, the proximal tool engaging portion of the set screw is a break-off type set screw that severs from a distal portion of the set screw when the distal portion is firmly seated relative to the anchor and the connecting member and sufficient torque is applied to the proximal tool engaging portion. A shaft 204 extends proximally from distal end 208 to a proximal handle 202. Handle 202 can be removably or permanently affixed to shaft 204. A sleeve 206 is rotatably mounted to shaft 204 with bushings, bearings or other suitable mechanism to allow sleeve 206 to rotate relative to shaft 204. Sleeve 206 provides a platform that can be grasped by the surgeon or other attendant to facilitate application of compressive or distractive forces between anchors while also allowing plug drive 230 to be rotated with handle 202 to firmly engage the connecting element with the plug while the compressive or distractive forces are maintained.

In another embodiment, sleeve 206 can be provided with a distal end configured to function as a counter-torque. In this embodiment, plug driver 200 includes a distal end opening with a shape that is complementary to and non-rotatably receives an external hex-shaped element of the extender. Sleeve 206 can then be grasped to prevent the extender from twisting or rotating as shaft 204 is rotated with handle 202 within sleeve 206 to tighten the plug against the connecting element and sever any break-off element of the plug that may be provided.

Each of the drivers 200, 230 includes shaft sized for insertion through the passage of the engaging member 52, 152 of the respective extender. The shafts are provided with lengths that allow the handles to be positioned proximally of the extender when the distal ends of the drivers 200, 230 are engaged to the plug or to the anchor.

In FIG. 29 there is shown a compressor 300. Compressor 300 includes an elongated body 302 and a pair of spaced arms 304 extending from a distal end 303 of body 302. Arms 302 form an opening 310 therebetween. An engaging member 306 at the distal ends of arms 304 extends between arms 304. Engaging member 306 includes a recess 308 to accommodate positioning of the connecting member therein. As shown in FIG. 29A, body 302 includes a C-shaped channel in cross-section that opens in a first direction. Engaging member 306 includes a shape that forms any suitably sized and shaped receptacle for positioning about the anchor, the receptacle opening in the direction opposite the channel of body 302.

In use, as shown in FIG. 1 and FIG. 44, compressor 300 is positioned so that at least one of the extenders is received through opening 310. In the illustrated embodiments of FIG. 1, extenders 150 and 250 are received through opening 310, and in FIG. 44 extenders 150 and 50 are received through opening 310. However, it is contemplated that one of the extenders, such as extender 50 in FIG. 48, can be removed prior to placement of compressor 300 about the other extender 150. In either case, body 302 is positioned with its distal end 303 against the extender 150 (extender 250 in FIG. 1) and/or reduction instrument 400 that remains. Engaging member 306 is mounted so that it extends around the anchor spaced from the anchor to which 150 (extender 250 in FIG. 1), which anchor is anchor 120 in FIGS. 44 and 48. The connecting member extending between the anchors can be received in recess 308 so that engaging member 306 can be firmly positioned about respective anchor to prevent it from slipping therefrom. The C-shape channel of body 302 receives extender and/or reduction instrument against which distal end 303 is positioned as compressor 300 is pivoted relative to and toward the respective extender.

Figure 48:
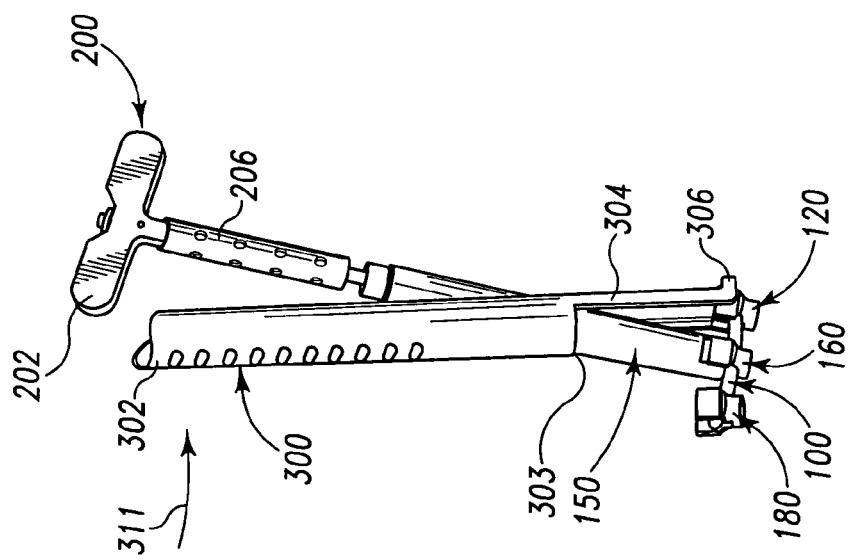
FIG. 48 shows the compressor of FIG. 29 positioned around the second extender and engaged to the first anchor with the first extender removed to deliver a compressive force between the first and second anchors (third extender not shown for clarity.)

When positioned as shown in FIGS. 44 and 48, body 302 can be pivoted in the direction indicated by arrow 311. Distal end 303 pivots about extender 150/reduction instrument 400, which act as a fulcrum, to move engaging member 306 and thus anchor 120 toward anchor 160. This results in a compressive force to move the adjacent vertebrae toward one another before final attachment of the connecting member to the anchors. It is contemplated that the connecting member can be firmly engaged to one of the anchors with a plug prior to compression of the adjacent vertebrae, and then secured to the other anchor after compression of the adjacent vertebrae to maintain the relative positioning between the vertebrae. For example, if one of the extender is removed prior to application of the compressive force, such as shown in FIG. 48, then the connecting member can be finally attached to anchor 120 prior to removal of extender 50. Plug driver 200 is positioned through extender 150 and sleeve 206 extends proximally therefrom. The surgeon or attendant can grasp sleeve 206 to provide leverage in moving compressor 300 and extender 150/plug driver 200 toward one another. When the desired compression is obtained, the plug in extender 150 can be finally tightened against the connecting member with plug driver 200. Since sleeve 206 rotates relative to shaft 202, compression can be maintained during plug tightening by grasping sleeve 206 and compressor 300.

In FIGS. 30 and 30A there is shown a distractor 320. Distractor 320 includes an elongated body 322, a distal angled portion 324 extending distally from body 322, and a distal arm 326 extending distally from distal angled portion 324. Distal arm 326 includes a recess 328 to accommodate positioning of the connecting member therein. Body 322 and distal angled extension 324 include a C-shaped channel extending therealong.

In use, distractor 320 is positioned with distal arm 326 against one anchor, such as anchor 160, and the C-shaped channel of body 322 is positioned toward the extender 50 extending from an adjacent anchor, such as anchor 120. It is further contemplated that the orientation of distractor 320 could be reversed to that arm 326 is positioned against anchor 120 and body 322 is positioned toward extender 150. It is also contemplated that distractor 320 can be positioned between anchors 160, 180 to distract the vertebrae to which these anchors are engaged. In any orientation, the extender extending from the anchor against which distal arm 326 is positioned can be removed prior to placement of distractor 320, or can remain mounted to the respective anchor during distraction. If the extender is removed, then the connecting member can be finally attached to the respective anchor prior to removal of the extender and prior to application of the distractive force.

The fulcrum area 327 formed at the junction between body 322 and distal angled extension 324 is positioned against the adjacent extender, with body 322 extending away from the adjacent extender so that its proximal end is spaced from the adjacent extender. As the proximal end of body 322 is moved toward the extender, distractor 320 pivots about fulcrum area 327 relative to the extender, and arm 326 is leveraged off of the extender 50 to move the respective anchors away from one another, thus distracting the vertebrae to which the anchors are engaged. When the desired positioning of the vertebrae has been achieved through distraction, the connecting member is finally attached to the anchors upon which the extender is mounted and form which distractor 320 is leverage to maintain the positioning between the vertebrae.

Compressor 300 and distractor 320 are also described in U.S. patent application Ser. No. 10/885,265, filed Jul. 6, 2004), which is incorporated herein by reference in its entirety.

In FIG. 31 there is shown a measuring device in the form of calipers 340. Calipers 340 include a first member 342 having a first body 343 and a first arm 344 extending transversely from first body 343. A second member 346 includes a second body 347 and a second arm 348 extending from second body 347. Second body 347 is slidably positioned and engaged about first body 343 and movable therealong to adjust a distance between the parallel arms 344, 348. Arms 344, 348 are elongated and sized to fit within the proximal end openings of the passages of the outermost extenders, such as extenders 50, 250. First body 343 includes indicia 350 therealong that provide indication of a connecting member length for positioning between the anchors to which extenders 50, 250 are mounted. In one embodiment, the indicia is correlated so that the indicated connecting member length is greater than the separation distance between the extenders to ensure that the connecting member extends through the receiver members of the anchors when positioned therein.

This separation distance can be used to select a connecting member of appropriate length to extend between the anchors at the distal ends of the outermost extenders. In one embodiment, extenders 50, 150 and 250 are pivotal relative to the anchors, and can be manipulated so that their proximal ends are positioned adjacent one another or moved away from one another. To measure the distance between anchors at the distal ends of the extenders, the extenders are manipulated to extend generally parallel to one another. Calipers 340 are then positioned in the proximal end openings of the passages of extenders 50, 250 to measure the length of the connecting member to extend between anchors 120 and 180.

Referring now to FIG. 32, extenders 50, 150, 250 are shown attached to anchors 120, 160, 180, respectively. Anchors 120, 160, 180 can be substantially identical to one another, although the use of differing types of anchors is also contemplated. Each of the anchors 120, 160, 180 includes a fastening portion 130 engaged to respective one of the vertebrae 132, 134, 136 and a receiver member 122 coupled to fastener portion 130. As shown in FIGS. 20-22, receiver member 122 can include a lower hole 128 extending therethrough through which the fastener portion 130 extends. The head or upper portion of the fastener portion can be pivotally captured in receiver member 122 with its lower portion extending through hole 128 for engagement to the vertebra. In one embodiment, anchors, 120, 160, 180 are multi-axial screws having a screw member pivotally coupled in a U-shaped saddle or receiver member 122. In this form, the receiver member 122 is pivotal about the head of the screw member when the threaded shaft of the screw member is engaged to the respective vertebra. Examples of multi-axial screw type anchors include the CD HORIZON® M-8 and M10 Multi-Axial Screws and the screws of the CD HORIZON® LEGACY™ Spinal System, all sold by Medtronic Sofamor Danek, Inc. It should be understood, however, that other anchors are contemplated, including those that are uniaxial in form, and that include means other than a bone screw for engaging the vertebrae, such as hooks, pins, staples, plates, interbody devices and cages, rivets, and suture anchors, for example. Furthermore, the receiver members can include any suitable form or structure for engagement with a connecting member.

Each of the receiver members 122 includes a pair of arms 124 defining a receptacle 126 therebetween. A connecting member, such as connecting member 100 discussed above, is positionable into the receptacle 126 between arms 124, and can extend from the receptacle to the next adjacent anchor. When the receiver member 122 is engaged to one of the extenders 50, 150, 250, receptacle 126 is in communication with the passage of the respective extender engaged thereto. Arms 124 can be internally threaded to threadingly engage an externally threaded set screw or plug positionable between arms 124. When engaged to arms 124, the plug securely clamps or holds the connecting member along a lower surface 127 of receiver member 122 that extends between arms 124.

Referring to FIG. 32, each of the extenders 50, 150, 250 can be attached to the corresponding anchor 120, 160, 180 either prior to engagement of the anchor with the corresponding vertebra, as discussed above, or after the anchor has been positioned in engagement with the vertebra. For example, one embodiment of a procedure contemplates an incision over the target location of the spinal column, and that the skin and tissue are sequentially dilated to provide a minimally invasive pathway for anchor insertion and engagement to each vertebra. The respective extender is then attached to the inserted anchor.

In another procedure, a cannulated outer needle with an inner stylet can first be inserted to the targeted regions of the vertebra, such as the pedicle in a posterior procedure, and aligned to provide the desired trajectory into the pedicle. Alignment can be monitored and checked with any viewing system, including radiographic, fluoroscopic, microscopic, endoscopic, loupes, naked eye, or any other suitable viewing system or instrument. After the cannulated needle and stylet are inserted into the vertebra, the inner stylet is withdrawn with the cannulated outer needle remaining engaged to the vertebra. A guidewire is positioned through the cannulated outer needle and engaged in the vertebra. The outer needle is then withdrawn so that the guidewire remains in place. The tissue around the guidewire is sequentially dilated with a number of tubular dilators of increasing diameter. When desired opening size is obtained, the guidewire and inner dilators are removed and the last inserted dilator provides a protected pathway to the pedicle or other targeted portion of the vertebra. The anchor can then be positioned through the dilated pathway and engaged to the vertebra. The corresponding extender 50, 150, or 250 is then attached to the receiver member of the anchor as discussed above, and the dilator is removed. The procedure is then repeated to position the desired number of extenders, whether it be two, three or four or more extenders. Incisions are made between the adjacent extenders to provide a pathway for insertion of the connecting member.

In another embodiment, the anchor and extender are inserted percutaneously without sequential dilation. The guidewire is positioned as discussed above, and the anchor can be cannulated for positioning over the guidewire. The anchor and extender are assembled and then positioned together over the guidewire, which guides the anchor to the pedicle or other targeted portion of the vertebra. A cannulated driver tool is positioned over the guidewire and through the extender to engage the head of the anchor and drive it into the vertebra.

In another embodiment, a pathway to the target location is prepared as discussed above. The guidewire and any dilators are removed. A cannula or other suitable retractor may remain in the incision to provide a protected pathway to the target location, although direct insertion through a micro-incision is also contemplated. The anchor is engaged to the extender, and an anchor driver such as anchor driver 230 is inserted through the extender and engaged to the head of the screw portion of the anchor. Anchor driver 230 maintains the screw portion in rigid alignment with the axis of the extender. The anchor and extender are inserted percutaneously to the target location of the vertebra, such as the pedicle. Insertion and alignment of the anchor may be monitored fluoroscopically or with any suitable surgical navigation system. The screw portion of the anchor is then engaged to the vertebra at the target location with the extender attached to the receiver member. Anchor and extender insertion and engagement is repeated for each vertebra, and an incision is made between adjacent ones of the extenders to provide an insertion path for the connecting element.

In any embodiment, placement of the anchors and extenders can be conducted through a micro-incision, through a retracted opening formed in the tissue approaching the targeted location on the vertebra, or through a tubular member providing a protected passageway to one or more of the adjacent vertebrae. Anchor driver 230 can be inserted through the extender and engaged to the anchor. In one embodiment, the anchor can be engaged to the spinal column while the extender remains engaged thereto since the anchor includes a screw portion rotatably received in the receiver member. The anchor driver engages the screw portion and can be rotated to rotate the screw portion in the receiver member to threadingly advance it into the bony structure of the spinal column.

It is also contemplated that nerve monitoring can be performed through the extenders to guide placement of the anchors in the appropriate locations in the vertebrae. In one embodiment, the anchors are engaged to pedicles of the respective vertebrae. Each pedicle can be drilled and, if necessary or desired, taped to receive a threaded screw portion of the anchor. Formation and tapping of the holes in the pedicles can be monitored with an electrical stimulus applied through a guidewire, tap, probe, or anchor driver prior to and during anchor insertion. Response of the patient can be monitored to determine that screw placement does not impinge upon any nerves. The guidewire, tap, probe, driver or other instrument can be placed through a sleeve or dilator made from plastic material to provide a non-conductive insulator. In still a further form, an electrical signal is applied through the extender to guide placement of the extender and anchor to the vertebrae without impinging on neural structures. The extenders can be insulated with a protective, non-conductive coating, sleeve or other layer to prevent the current from straying.

When the anchors are engaged to the vertebrae and the extenders are attached to the anchors, the extenders extend through the skin and tissue so that their proximal ends, including at least entry hole 78 or 84, is accessible for insertion of a connecting member. In FIG. 33 extenders 50, 150, 250 are shown engaged to the receiver members of anchors 120, 160, 180. It should be understood, however, that any one or combination of the extender embodiments discussed herein may be secured to anchors 120, 160, 180. Fastener portions 130 and vertebrae 132, 134, 136 have been omitted from FIGS. 33-37, 41-45 and 47, it being understood that the anchors 120, 160 180 in each of these figures can be provided with a fastening portion 130 engaged to vertebrae 132, 134, 136. In FIG. 33 extender 50 is shown with entry hole 84 in the actuator. Entry hole 84 is oriented away from the other extenders 150, 250. It should be understood that extender 50 may employ an actuator 70 with entry hole 78 and an engaging member with an entry hole 66 offset proximally of the proximal terminal ends of the slots of the extenders. In either embodiment, the elongated slot 51 (FIG. 41) defined by the engaging member 52 and actuator 70 of extender 50 is positioned to open toward the aligned elongated slots 151 of the next adjacent extender 150. Similarly, the elongated slot 251 of extender 250 is oriented toward and aligned with slots 151 of extender 150. The blind or solid end of extender 250 is oriented away from extender 150.

Figure 35:
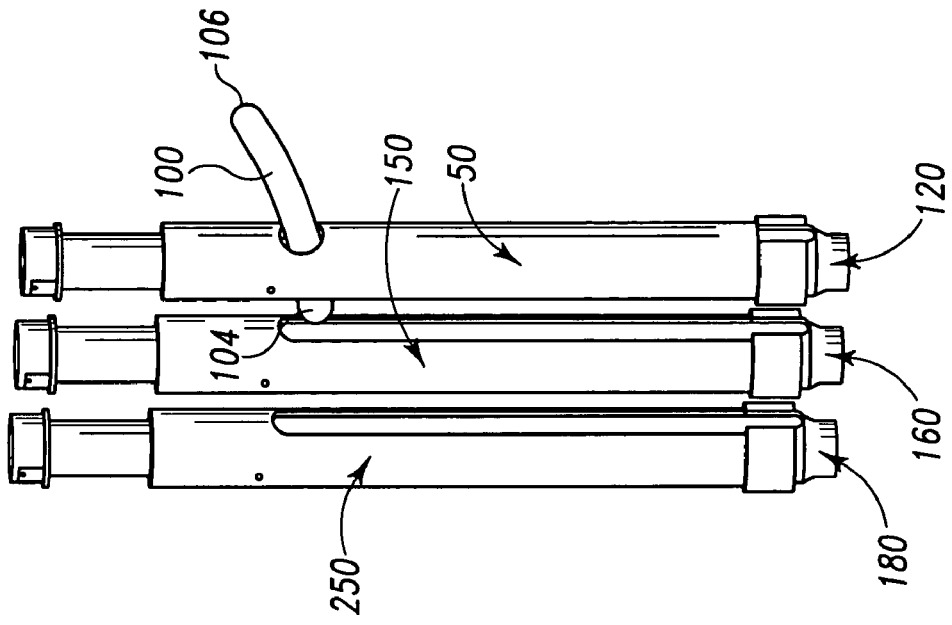
FIG. 35 is a view showing the connecting member inserted through the first extender and approaching the second extender.
Figure 34:
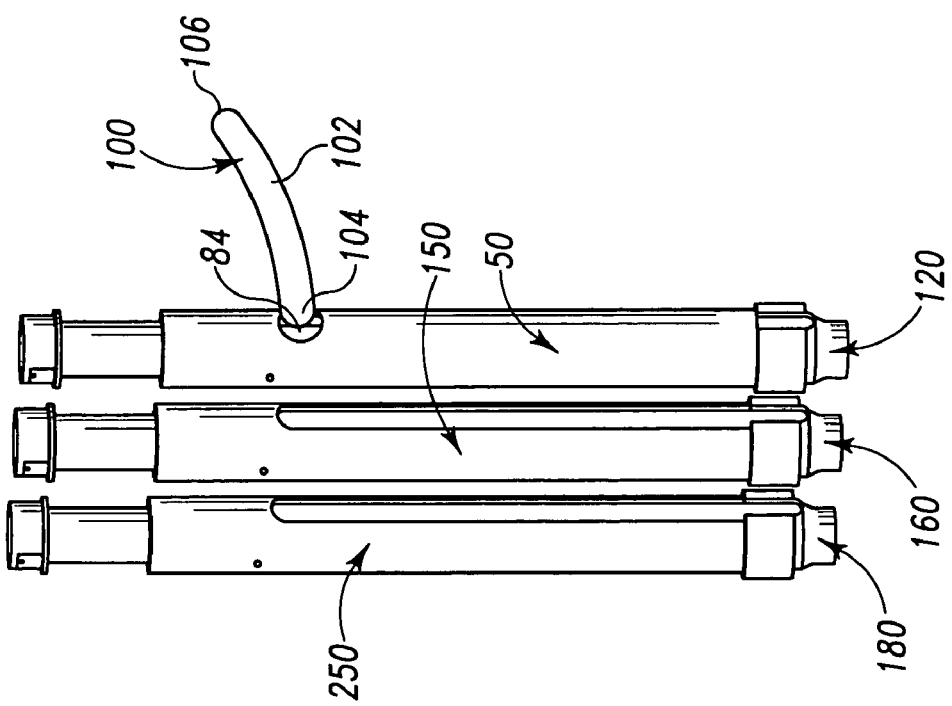
FIG. 34 is a view showing a connecting member before loading into the extenders of FIG. 32.

In FIG. 34, connecting member 100 is positioned for insertion through entry hole 84 along an initial insertion path. In the illustrated embodiment, connecting member 100 is shown, it being understood that any other connecting member embodiment could be employed, so long as it is positionable between at least two of the extenders 50, 150, 250. In FIG. 35, connecting member 100 is positioned further along the initial insertion path and through first extender 50 with its leading end 104 positioned near the adjacent one of the aligned slots 151 of second extender 150. In embodiments where the receiver member of the anchor is pivotally adjustable relative to the fastening portion of the anchor, extender 150 can be manipulated if necessary to align the elongated slots 151 of extender 150 with the leading insertion end 104 of connecting member 100.

Figure 37:
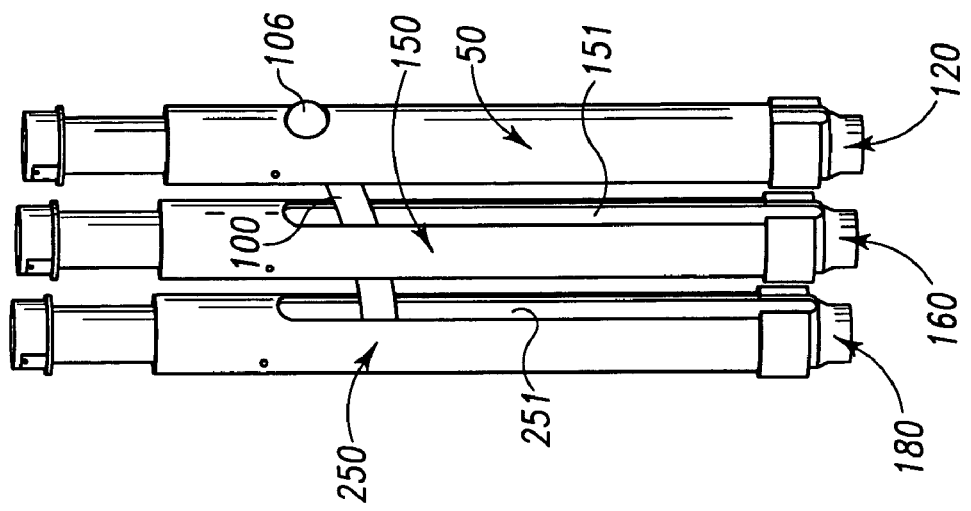
FIG. 37 is a view showing the connecting member inserted through the first, second and third extenders.
Figure 36:
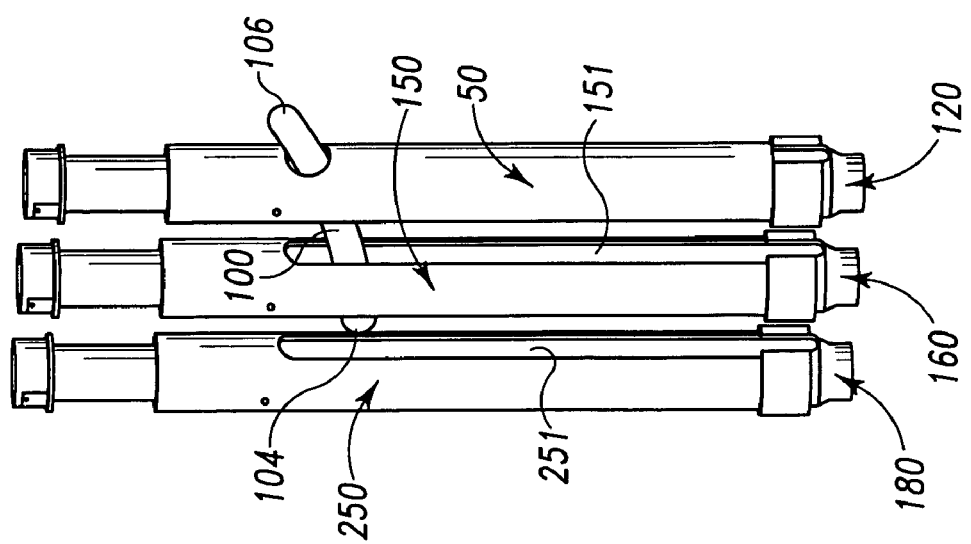
FIG. 36 is a view showing the connecting member inserted through the first and second extenders and approaching the third extender.

In FIG. 36, connecting member 100 is positioned further along the initial insertion path through the aligned slots 151 of second extender 150, and its leading end is positioned adjacent the aligned slot 251 of third extender 250. In FIG. 37 connecting member 100 is advanced further along the initial insertion path so that its leading end 104 is positioned through the aligned slot 251 of third extender 250. The trailing end 106 of connecting member 100 is positioned for delivery through the entry hole 84 of first extender 50.

As shown in further detail in FIG. 38, second end 106 of connecting member 100 is received in passage 58 of engaging member 52 after positioning through entry hole 84 of actuator 70 and the aligned proximal end 67 of slot 60 of engaging member 52 of extender 50. Body 102 extends through the opposite elongated slot 51 of extender 50. In the illustrated embodiment, first end 104 and second end 106 of connecting member 100 are constrained in passages of extenders 50, 250 since neither end can pass through the side of extender 50 opposite slot 51 or the side of extender 250 opposite slot 251, each of which includes a blind end formed by the wall of the respective actuator. Accordingly, connecting member 100 cannot slip or be moved out of passage 58 until first end 104 and second end 106 is advanced through the distal end opening of extenders 50, 250 adjacent the receiver member of anchors 120, 180.

Figure 39:
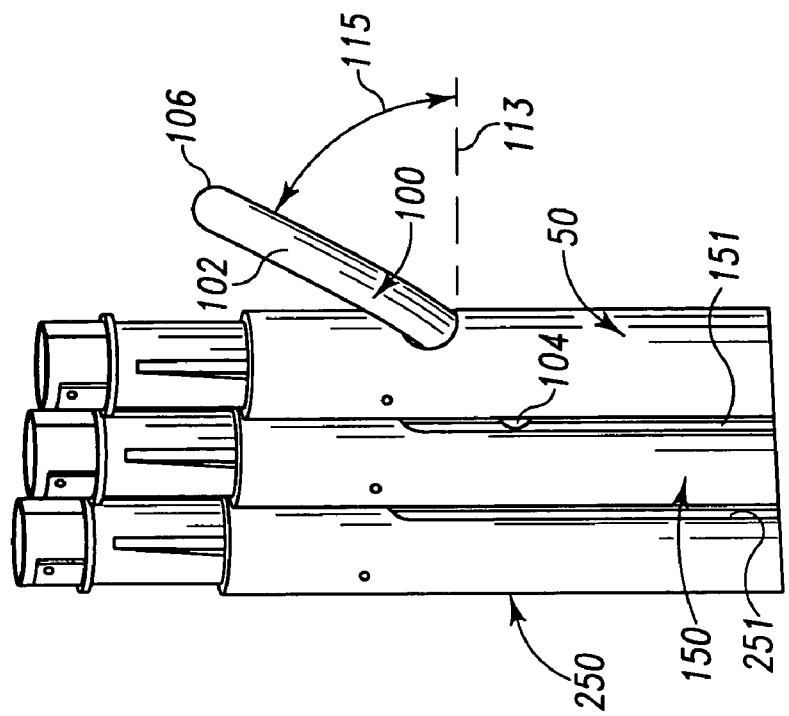
FIG. 39 is a view of the proximal portions of the extenders showing an alternate approach of the connecting member into the extenders.

FIG. 39 shows an alternate approach for connecting member 100 or any other connecting member embodiment in its delivery through extenders 50, 150, 250. If extenders are mounted on anchors 120, 160, 180 having multi-axial capabilities, extenders 50, 150, 250 can be manipulated so that their proximal ends are positioned adjacent one another. Extenders 50, 150, 250 define an axis 113 extending generally parallel to the proximal terminal ends of the aligned slots of the extenders 50, 150, 250. When the proximal ends of the extenders are positioned adjacent one another, the length between the extenders will be less along axis 113 than the length between the anchors mounted to their distal ends. Since connecting member 100 includes a length to extend between the anchors engaged to the distal ends of the extenders, it is too long to positioning between extenders 50, 150, 250 along axis 113.

Connecting member 100 can be inserted through entry hole 84 at a steep angle 115 relative to axis 113. In this approach, the effective length of connecting member 100 along axis 113 is reduced at least upon initial insertion, allowing its opposite ends 104, 106 to fit within the space between extenders 50, 250 adjacent their proximal ends. As connecting member 100 is advanced distally, trailing end 106 can be moved distally relative to leading end 104 to oriented body 102 generally parallel to axis 113 for receipt into the receiver members of anchors 120, 160, 180.

As shown in FIGS. 40-43, connecting member 100 is advanced distally along elongated slots 51, 151, 251 of extenders 50, 150, 250 to anchors 120, 160, 180, respectively. The angulation of connecting member 100, if any, is decreased until connecting member 100 is seated adjacent the receiver members of anchors 120, 160, 180. Connecting member 100 can be advanced distally toward the anchors using any technique. For example, holder 134 can be inserted between extenders so that its grasping mechanism 140 grips connecting member 100. Holder 134 can then be manipulated by the surgeon to advance and seat connecting member 100 in the receiver members of the anchors 120, 160, 180. Plug driver 200 can then be fitted with a plug or set screw, and employed to deliver the plug through the passage of one of the extenders to engage the connecting member in the receiver member of the anchor. Plug driver 200 is then employed through the remaining extenders to engage plugs to the remaining anchors.

It may also be desirable to provide a desired alignment between vertebrae by reducing the connecting member into the receiver members of the anchors. For example, the vertebrae may be misaligned as a result of spondylolisthesis, anatomical differences between the vertebrae, or some other condition. Also, there may be slight misalignments between the receiver members that make manually positioning the connecting member into each of the receiver members difficult, even if holder 134 is employed. In such situations, reduction instrument 400 can be employed to provide a mechanical advantage to seat the connecting member in the receiver members of the anchors 120, 160, 180.

FIGS. 40-43 show reduction instrument 400, which can be positioned over any one of the extenders 50, 150, 250 to contact connecting member 100 and advance and seat connecting member 100 in the anchors. Reduction instrument 400 includes a tubular reduction member 402 having a pair of reduction arms 404 extending distally therefrom. Reduction member 402 includes an inner passage sized to receive one of the extenders 50, 150, 250 therethrough. An actuator including a first handle 406 and a second handle 408 is provided at the proximal end of reduction member 402. Second handle 408 is pivotally coupled to reduction member 402 at 410, and a locking collar 414 extends from first handle 406, as shown in FIG. 42A. The locking collar 414 is housed within reduction member 402. First handle 406 extends through the proximal end slot 416 formed in reduction member 402. Locking collar 414 includes a projecting portion 418 structured to releasably engage, for example, proximal collar 62 of engaging member 52. Locking collar 414 includes a length along reduction member 402 that is about the same length as proximal collar 62.

As shown in FIG. 23, one embodiment of proximal collar 62 includes a recessed portion 87 having an undercut portion 88. Undercut portion 88 forms a lip 89 around a portion of the upper proximal end of proximal collar 62. Locking collar 414 is positionable about proximal collar 62, and projecting portion 418 is received into the recessed portion 87 adjacent undercut portion 88. When reduction instrument 400 is rotated counterclockwise, projecting portion 418 is moved into undercut portion 88, and lip 89 projecting therefrom engages projecting portion 418 to securely mount reduction instrument 400 to engaging member 52 in a bayonet type locking arrangement. It should be understood that each of the extenders 50, 150, 250 can be provided with a proximal collar engageable with reduction instrument 400. Proximal collar 62 may also be configured as shown, for example, FIGS. 4-7, in which collar 62 does not include recessed and undercut portions 87, 88.

Other embodiments contemplate other means for engaging reduction instrument 400 to extenders 50, 150, 250, including fasteners extending between reduction instrument 400 and the extender, interference fits between reduction instrument 400 and the extender, and threaded engagement between the reduction instrument and extender, to name a few.

Figure 41:
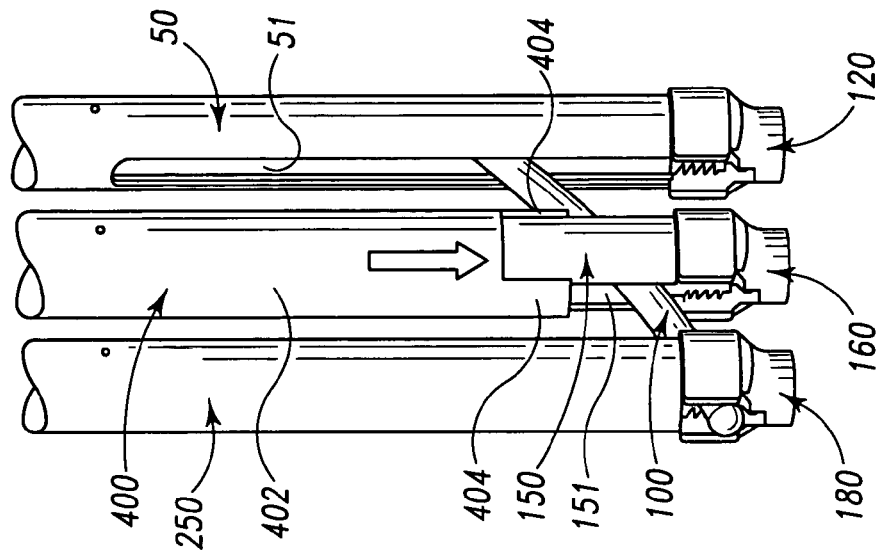
FIG. 41 shows the reduction instrument being manipulated relative to the second extender to advance the connecting member toward the anchors.

In FIG. 40 reduction instrument 400 is positioned over second extender 150, it being understood, however, that reduction instrument could be positioned over any of the other extenders 50, 250 as well. The actuating mechanism of reduction instrument 400 is unactuated as indicated by the relative separation between first and second handles 406, 408. Further, locking collar 414 is not yet seated on proximal collar 62. In FIG. 41 reduction instrument 400 is advanced distally along extender 150 so that reduction arms 404 contact connecting member 100. The reduction arms move connecting member 100 distally along the extenders 50, 150, 250 toward the anchors 120, 160, 180. In FIG. 42, reduction instrument 400 is advanced distally along extender 150 until its locking collar 414 is aligned with proximal collar 62. Reduction instrument is rotated clockwise relative to its FIG. 40 position so that the locking collar 414 engages the proximal collar 62 with the bayonet-type fit, as discussed above.

With first handle 406 and the locking collar 414 locked to extender 150, the second handle 408 can be pivoted about 410 to move reduction member 402 distally, as shown in FIGS. 42 and 43, along extender 150. This distal movement of reduction member 402 moves reduction arms 404 distally against connecting member 100. Locking collar 414 engages the proximal collar 62 of extender 150, and pushes thereagainst to supply the needed force to move connecting member 100 into the receiver members of the anchors. The reduction of connecting member 100 can be continued until connecting member 100 is firmly seated against the bottom surfaces of the anchors. When final reduction has been obtained, a set screw or plug can be delivered through extender 150 to engage connecting member 100 to anchor 160. Reduction instrument 400 can then be placed over none, one or both of the other extenders 50, 250 to finally reduce connecting member 100 into the receiver members of these anchors. Reduction instrument 400 can hold the connecting member 100 in the reduced position during engagement of the plug with the anchor, such as shown with plug driver 200 in extender 50 in FIG. 45. The handles 406, 408 of reduction instrument 400 can be firmly grasped to act as a counter-torque during engagement of the plug to prevent the receiver member of the anchor from rotating as the plug is engaged with the desired torque.

Compression or distraction of the vertebrae can also be achieved prior to engaging connecting member to each of the anchors. In FIG. 44 there is shown compressor 300 positioned so that extenders 50, 150 are received through opening 310. Engaging member 306 is positioned about anchor 120, and distal end 303 of body 302 contacts reduction instrument 400 positioned about extender 150. Compressor 300 is pivoted in the direction indicated by arrow 311 to compress the vertebrae engaged by anchors 120, 160. When the desired compression has been obtained, plugs delivered through the extenders with plug driver 200 are secured to the anchors to engage connecting member 100 to the anchors and maintain the compressed condition between the vertebrae. It is further contemplated that connecting member 100 can be secured to the receiver member of one of the anchors 120, 160 prior to delivery of the compressive force, and then connecting member 100 secured to the other anchor while compressor 300 maintains the compressive force. Compressor 300 can then be re-positioned to deliver a compressive force between anchor 180 and anchor 160 if desired. In a similar manner, distractor 320 can be employed to engage one of the anchors 120, 160, 180 and an adjacent extender to distract the adjacent vertebrae prior to securing the connecting member to adjacent anchors, as discussed above.

When the connecting member is positioned in, on or about the receiver members, plug driver 200 is mounted with a plug, which is delivered through each of the extenders 50, 150, 250 and engaged to the receiver member of the anchor to engage the connecting member thereto. As shown in FIG. 1, a counter-torque device 220, such as a wrench, includes a head 224 engageable with the extender. Handle 222 extends from the head 224, and can be grasped to prevent the extender and receiver member of the anchor engaged to the extender from rotating during engagement of the plug with the receiver member. In the embodiment shown in FIGS. 1-3, the actuator of the extenders 50, 150, 250 include a number of flats adjacent its proximal end to facilitate engagement by the head of counter-torque device 220. Other embodiments contemplate that the proximal end of the actuators are cylindrical, as shown in FIGS. 8-17, for example. In such embodiments, reduction instrument 400 can be employed as a counter-torque device, or some other means for holding the position of the extender may be employed.

Figure 47:
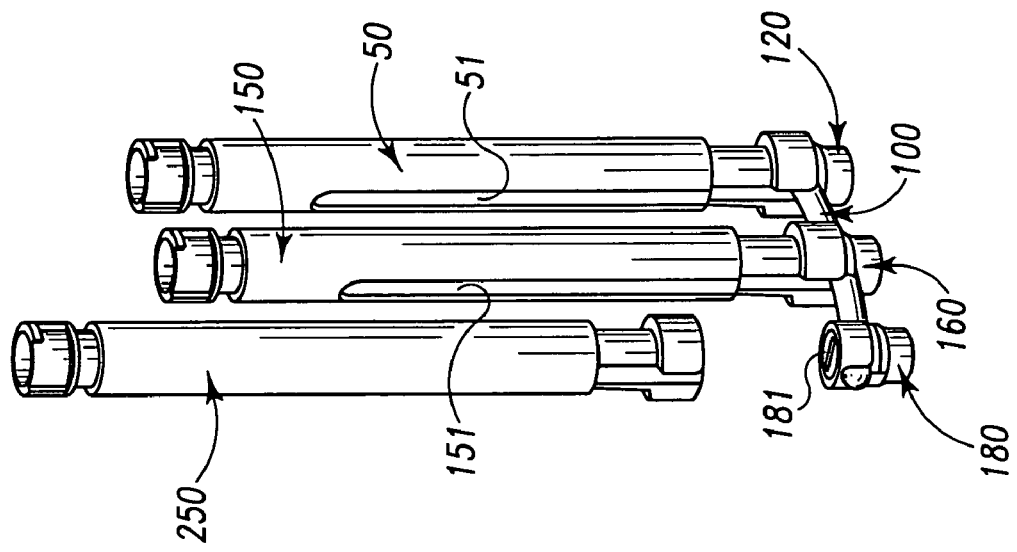
FIG. 47 shows removal of the third extender from the third anchor.
Figure 46:
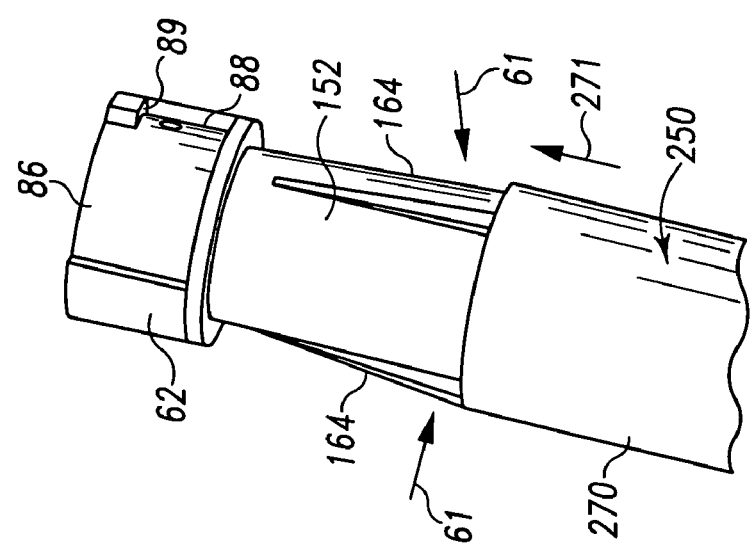
FIG. 46 is a perspective view of the proximal portion of the third extender showing release of the actuator from the engaging member.

When connecting member 100 is finally secured to anchors 120, 160, 180, anchor extenders 50, 150, 250 can be removed from the respective anchors. Extenders 50, 150, 250 can be removed together after securement of the connecting member to all of the anchors, or extenders 50, 150, 250 can be removed sequentially with each extender being removed after securement of the connecting member to the anchor in which the respective extender is mounted. As shown in FIG. 46, tabs 164 of engaging member 152 are pressed inwardly as indicated by arrows 61 so that their distal ends no longer engage the proximal end of the corresponding actuator 270. Actuator 270 may then freely slide proximally relative to engaging member 152 in the direction indicated by arrow 271, allowing the feet 156 of engaging member 152 to be released from their clamping position about the receiver member of anchor 180, as shown in FIG. 47. Extender 250 may then be withdrawn from the surgical site. The process is repeated for each of the other extenders 50, 150. The minimally invasive wound created to accommodate insertion of extenders 50, 150, 250 can then be dressed and closed as may be appropriate.

While extenders 50, 150, 250 have been shown as having circular cross-sections, extenders with non-circular cross-sections are also contemplated. The elongated slots of the extenders need not be the same length along the same extender, nor does each extender have to be provided with one or more elongated slots that are the same length as the slots of the other extenders. The actuator and engaging member of the extenders may be a one-piece component. The extenders may also include surface features to facilitate engagement of the reduction instrument therewith. For example, the actuator may be provided with ratchet teeth along its outer surface to engage a pawl or teeth of a ratcheting system of the reduction instrument, providing a mechanical advantage to leverage the reduction instrument distally into contact with the connect member to seat the connecting member in the anchors. In another embodiment, the reduction instrument includes an actuating assembly with a pair of handles that extend proximally from the reduction member rather than laterally as shown in the figures. In another embodiment, the reduction member 402 can be a collar at a distal end of a linkage extending between the actuating assembly and collar. The linkage is moveable with a handle assembly to move the reduction member 402 distally into contact with the connecting member. Still further, the reduction member need not extend about the extender, but rather can extend alongside the extender to which it is mounted.

Figure 49:
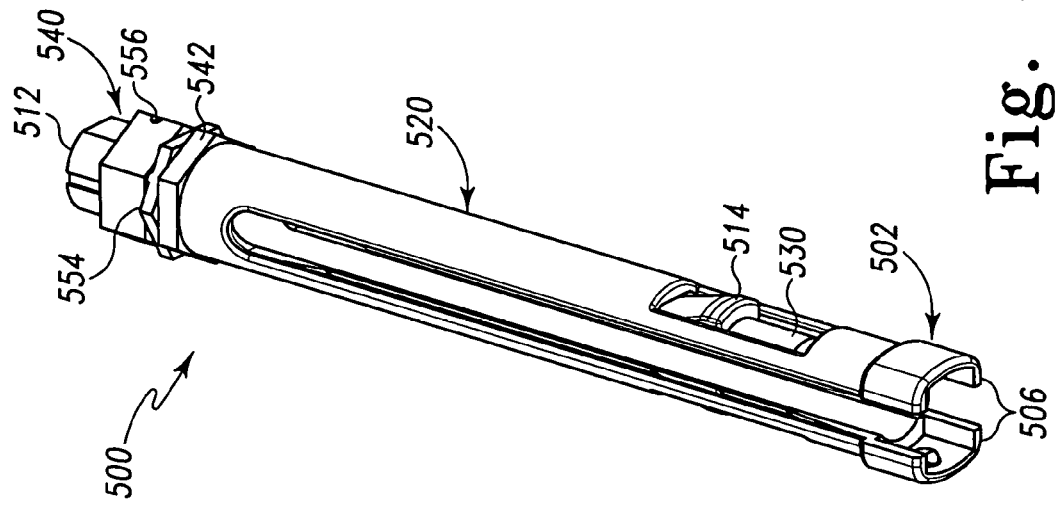
FIG. 49 is a perspective view of another embodiment extender.
Figure 50:
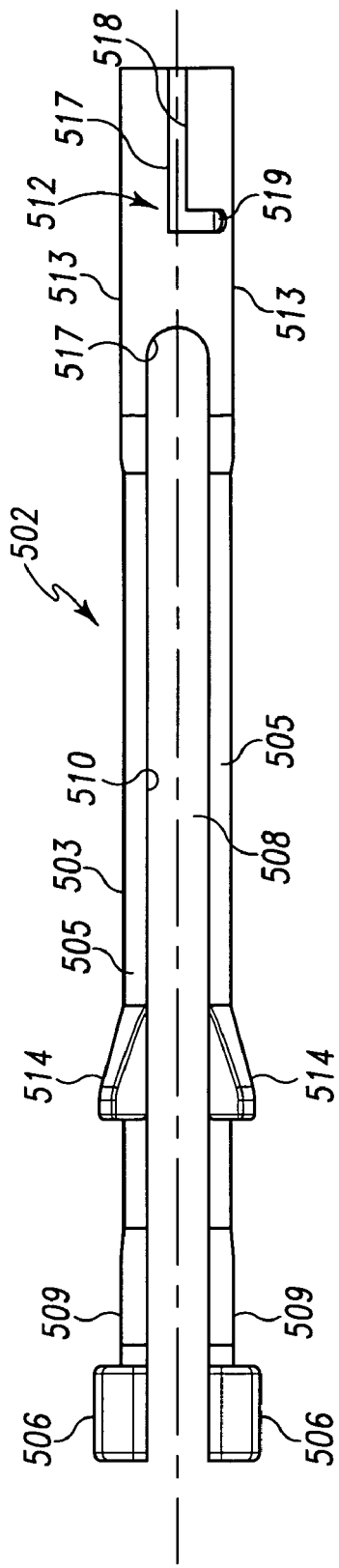
FIG. 50 is an elevation view of an engaging member comprising a portion of the extender of FIG. 49.
Figure 51:
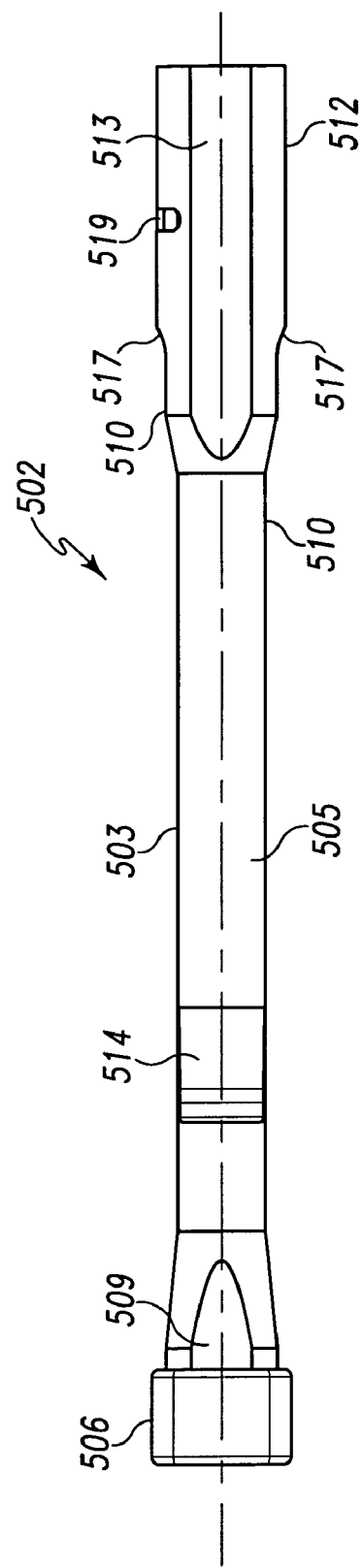
FIG. 51 is an elevation view of the engaging member of FIG. 50 rotated 90 degrees about its longitudinal axis from its FIG. 50 orientation.

Referring now to FIGS. 49-56, there is shown another embodiment extender 500 that can be employed with system 40 as discussed above with respect to extenders 50, 150, 250. In the illustrated embodiment, extender 500 includes an engaging member 502 housed within an actuator 520. As shown in FIGS. 50-51, engaging member 502 includes opposing feet 506 moveable toward and away from one another in response to a position of actuator 520 relative thereto. Engaging member 502 includes a body 503 extending between distal feet 506 and a proximal collar 512. Body 503 defines a passage 508 extending between and opening at the distal and proximal ends of body 503. Feet 506 may include inwardly facing projections for engagement with corresponding indentations formed in the opposite sides of a receiver member of an anchor, as discussed above with respect to engaging member 52.

Engaging member 502 further includes elongated slots 510 formed on opposite sides thereof which open passage 508 to the exterior of body 503 along a major portion of the length of body 503. Slots 510 have sufficient length so that the proximal terminal ends 517 of slots 510 can be accessed for delivery of the connecting member through the slots 510. Slots 510 extend distally from proximal terminal ends 517 and between feet 506 to facilitate delivery of a connecting member along slots 510 to the receiver member of the anchor engaged to feet 506. Opposing legs 505 extend proximally from feet 506 and along slots 510. Camming surfaces 509 extend along the outer surface of respective ones of the legs 505 from a maximum height adjacent the respective foot 506, and taper proximally along a portion of the length of the respective leg 505.

In the illustrated embodiment, slots 510 extend proximally a sufficient distance such that no entry hole is provided through one or both of the legs 505 for delivery of a connecting member. However, an entry hole may be provided through one or both of the legs 505 at a location proximal of the proximal terminal end 517 of one of the slots 510.

Engaging member 502 further includes tabs 514 projecting outwardly therefrom along respective ones of the legs 505 at a location spaced proximally of feet 506 and camming surfaces 509, but distally of the proximal terminal ends 517 of slots 510. Tabs 514 are integral with respective ones of the legs 505, and are tapered proximally to facilitate distal movement of actuator 520 along engaging member 502. Tabs 514 further each include a steeply slope or vertical distally oriented endwall that engages actuator 520 to limit proximal movement of actuator 520 relative to engaging member 502, as discussed further below. Legs 505 are movable toward one another by depressing tabs 514 to recess tabs 514 within actuator 520, allowing proximal movement of actuator 520 along engaging member 502.

Proximal collar 512 includes a rounded shape with opposing flat surfaces 513 extending therealong. One side of collar 512 includes a locking receptacle 518 extending from and opening at the proximal end of collar 512. Locking receptacle 518 includes an axial portion 517 extending in the proximal-distal directions along collar 512, and an offset portion 519 extending transversely to recessed portion 517 along the rounded portion of collar 512. In the illustrated embodiment, axial portion 517 and offset portion 519 are formed by grooves in the outer surface of collar 512, and do not communicate with passage 508. The end of offset portion 519 opposite axial portion 517 includes a through hole that communicates with passage 508. By providing a wall portion along locking receptacle 518, the rigidity of collar 512 is maintained. Other embodiments contemplate that all or a portion of locking receptacle 518 is formed by a slot extending through collar 512.

Actuator 520 is further shown in FIGS. 52-56. Actuator 520 includes a body 522 extending between a distal end 526 and a proximal end 524. A bore 536 extends between and opens at distal and proximal ends 526, 524. Bore 536 includes opposite windows 530 adjacent distal end 526 in communication with bore 536. Tabs 514 are received through windows 530 when engaging member 502 is assembled with actuator 520. As shown in FIG. 56, bore 536 includes a shape that matches the shape of collar 512 of engaging member 502. Flat surfaces 513 are received along corresponding flat surfaces 537 along bore 536 to ensure proper alignment of engaging member 502 in actuator 520 and also to prevent engaging member 502 from rotating relative to engaging member 520.

Actuator 520 further includes an elongate slot 532 extending along each side thereof from distal end 526 to a proximal terminal end 533 of each slot 532. Proximal terminal end 533 is spaced distally of proximal end 524. Other embodiments contemplate that actuator 520 includes a slot along only one side thereof. The opposite side of the actuator may include an entry hole, as discussed above with respect to actuator 70, or a solid wall as discussed above with respect to actuator 270; or a slot and an entry hole along one or both sides thereof.

Double-slotted extenders or extenders with opposing slots such as shown in FIGS. 3 and 49 may be employed in system 40 with the opposing or double-slotted extenders mounted to the intermediate anchors, such as anchor 160. Furthermore, the opposing or double-slotted extenders can also be employed with the extenders mounted to one or both of the outermost anchors 120, 180. Alternatively, the system 40 includes at least one extender having an actuator with an entry hole in one side thereof and a slot in at least the opposite side thereof. The entry hole/slotted extender can be mounted on one or both of the outermost anchors 120, 180, with the slotted side of the extender oriented to be adjacent a slot of the adjacent extender. In a further embodiment, the system 40 includes an extender with an actuator having a solid outer wall along one side thereof and a slot on the other side thereof. The single-slotted extender is mounted to one of the outermost anchors 120, 180. In this embodiment, a double-slotted or entry hole/slotted extender is mounted to the other of the outermost anchors 120, 180.

Actuator 520 further includes a locking mechanism 540 adjacent proximal end 522. Locking mechanism 540 includes a flange member 542 about proximal end 524 of actuator 520 and an extension 544 extending proximally from flange member 542. Extension 544 includes a locking receptacle 546 having an axial portion 548 and an offset portion 550. Offset portion extends 550 laterally from a distal end of axial portion 548 and radially about a portion of extension 544 about the longitudinal axis of actuator 520.

Locking mechanism 540 further includes a groove 552 formed in extension 544 in an outer surface thereof. Groove 552 extends proximally from and is in communication with offset portion 550. A locking collar 554 is positionable about extension 544 and rotatably captured thereon with an end member 556. Locking collar 554 includes an inwardly extending locking projection 558 that is positionable in locking receptacle 546. End member 556 is positionable about extension 544 with locking collar 554 rotatably captured between end member 556 and flange member 542. Pins 560 extend through end member 556 and engage it to extension 544. End member 556 further defines a groove 562 extending therealong from a distal end of end member 556 that is aligned with groove 552 of extension 544.

A ball member 564 and spring member 566 are captured between grooves 552, 562. Spring member 566 distally biases ball member 564 toward and into contact with locking collar 554. As shown in FIG. 53A, locking collar 554 includes a detent 568 adjacent locking projection 558 that receives ball member 564. When locking projection 558 is received in offset portion 550, ball member 564 is biased into engagement with detent 568 to maintain locking collar 554 in rotational position relative to extension 544.

To assemble engaging member 502 with actuator 520, locking collar 554 is rotated to align locking projection 558 with axial portion 548 of locking receptacle 546. The proximal end of engaging member 502 is loaded through the distal end opening of actuator 520, and advanced toward the proximal end of actuator 520 through bore 536 with flat surfaces 513 aligned with flats 537 along bore 536. Axial portion 517 of locking receptacle 518 is aligned with locking projection 558, which projects into bore 536. Engaging member 502 is advanced proximally relative to actuator 520 to position locking projection 558 in axial portion 517 of locking receptacle 518. Simultaneously, tabs 514 are positioned in alignment with corresponding ones of the windows 530 of actuator 520. Engaging member 502 is advanced further proximally relative to actuator 520 until tabs 514 contact or are positioned adjacent the proximal ends of windows 530, which also positions locking projection 558 adjacent offset portion 519 of locking receptacle 518. Locking collar 554 can then be rotated to position locking projection 558 into offset portion 550 of locking receptacle 546 and offset portion 519 of locking receptacle 518. This in turn allows spring member 566 to bias ball member 564 into detent 568 if locking collar 554, engaging locking collar 554 into a locking position. Locking projection 558 engages engaging member 502 in offset portion 519 to resist axial movement of engaging member 502 relative to actuator 520.

In its assembled and clamping position, extender 500 provides an avenue for insertion of a connecting member through one or more of the elongated slots defined by the assembly of engaging member 502 with actuator 520. Placement of the connecting member between two or more extenders mounted to two or more anchors and advancement of the connecting member along the extenders to the anchors can be conducted in the manner discussed above with respect to system 40.

When extender 500 is assembled, engaging member 502 is positioned in bore 536 of actuator 520. When locking mechanism 540 is in its unlocked position, i.e. locking projection 558 is aligned with axial portions 517, 548 of locking receptacles 518, 546, actuator 520 is movable distally and proximally relative to engaging member 502 to selectively engage and release an anchor positioned between feet 506. As actuator 520 is advanced distally relative to engaging member 502, tabs 514 contact the inner wall of actuator 520 along bore 536 and move feet 506 inwardly toward one another to allow passage of actuator 520 thereover. When tabs 514 are aligned with windows 530, legs 505 return toward their pre-insertion configuration so that tabs 514 project through adjacent ones of the windows 530. The inner wall of actuator 520 about bore 536 contacts camming surfaces 509 of engaging member 502, and feet 506 are located distally of distal end 526 and maintain feet 506 in engagement with an anchor positioned therebetween.

To release the anchor, the locking mechanism 540 is positioned to it unlocked position to allow actuator 520 and engaging member 502 to move relative to one another. Actuator 520 is moved proximally relative to engaging member 502 to move tabs 514 toward the distal ends of the respective windows 530, positioning the inner surface of actuator 520 proximally of camming surfaces 509. This allows feet 506 to move away from one another to release the anchor engaged therebetween. When released from the anchor, engaging member 502 can be withdrawn from actuator 520 to facilitate cleaning of the components of extender 500.

Figure 58:
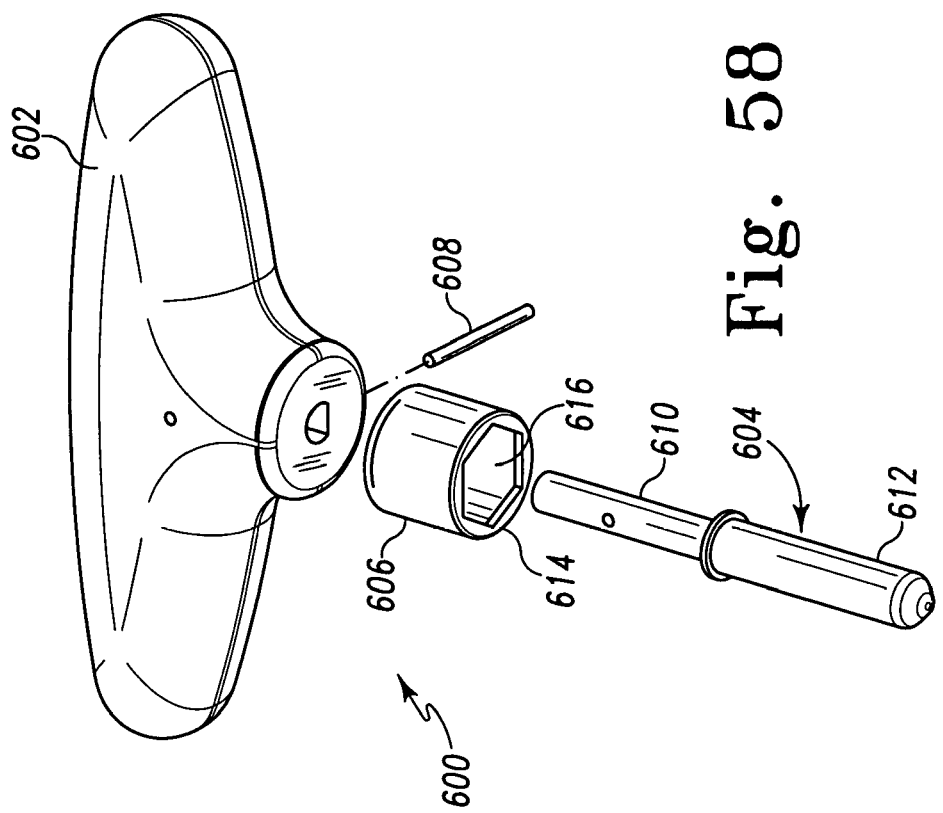
FIG. 58 is an exploded perspective view of the handle of FIG. 57.
Figure 57:
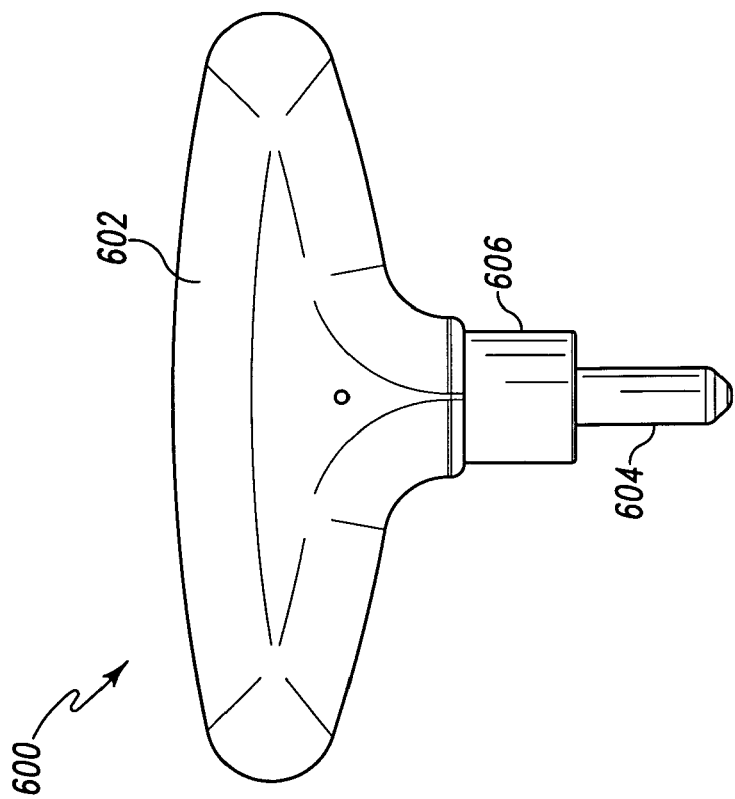
FIG. 57 is an elevation view of a handle engageable to the extender of FIG. 49.

To facilitate movement of locking collar 554 between its locking position aligned with offset portions 550, 519, a handle member 600 is provided as shown in FIGS. 57-58. Handle member 600 includes a handle portion 602 and a shaft portion 604. A receiving member 606 extends from handle portion 602 about shaft portion 604. As shown in FIG. 58, shaft portion 604 includes a lower portion 612 and an upper portion 610. Upper portion 610 is engaged to handle portion 602 with pin 608. Receiving member 606 is engaged to handle portion 602, and lower portion 612 of shaft portion 604 projects from receiving member 606, as shown in FIG. 56. Receiving member 606 includes an end member 614 that defines a shaped opening 616 that extends about and is spaced from shaft portion 604.

In use, handle member 600 is positionable relative to extender 500 so that lower shaft portion 612 is received in passage 508 of engaging member 502 adjacent proximal collar 512. End member 556 is received in receiving member 606 with end member 614 positioned about locking collar 554. The shaped opening 616 engages locking collar 554 in form fitting engagement, with receiving member 606 freely rotatable about end member 556. Accordingly, rotation of handle member 600 rotates locking collar 554 between it locking and unlocked positions. Handle portion 602 provides a mechanical advantage to overcome the bias of spring member 566 to move ball member 564 out of detent 568.

It should be understood, however, that locking collar 554 could also be moved manually between its locking and unlocking position. Locking collar 554 could also be provided so that at least a portion thereof projects outwardly from actuator 520 to facilitate grasping thereof. Other locking arrangements between the engaging member and actuator of the extender are also contemplated as discussed herein.

While the invention has been illustrated and described in detail in the drawings and foregoing description, the same is to be considered as illustrative and not restrictive in character, and that all changes and modifications that come within the spirit of the invention are desired to be protected.

What is claimed is:

1. A spinal surgical system, comprising:
    a first anchor engageable to a spinal column;
    a first extender extending between a proximal end and a distal end, said distal end being releasably engageable to said first anchor when engaged to the spinal column, said first extender including a passage extending at least partially therethrough and opening at said distal end, said first extender including an entry hole in one side thereof in communication with said passage and an elongated slot along another side thereof opposite said entry hole, said elongated slot being in communication with said passage and opening at said distal end;
    a second anchor engageable to the spinal column;
    a second extender extending between a proximal end and a distal end, said distal end being releasably engageable to said second anchor when engaged to the spinal column, said second extender including a passage extending at least partially therethrough and opening at said distal end, said second extender including an elongated slot in one side thereof in communication with said passage, said elongated slot of said second extender being alignable with said elongated slot of said first extender;
    a connecting member positionable through said entry hole of said first extender and into a position extending between said passages of said first and second extenders through said elongated slots of said first and second extender, wherein:
    at least one of said extenders includes an engaging member defining said passage, said engaging member being removably engageable with a respective one of said first and second anchors, said at least one extender further including an actuator positioned about said engaging member and movable therealong to bias said engaging member into engagement with said respective anchor;
    said engaging member includes a pair of opposite legs separated from one another by a pair of opposite slots, said slots each including a proximal terminal end spaced distally from a proximal end of said engaging member;

said actuator includes a tubular body positionable over said engaging member, said tubular body defining at least one slot extending therealong aligned with one of said slots of said engaging member to form said elongated slot of said at least one extender; and said actuator defines said entry hole in a side thereof opposite said at least one slot of said actuator, said entry hole being aligned with said proximal terminal end of said slots of said engaging member.

2. A spinal surgical system, comprising:

a first anchor engageable to a spinal column;

a first extender extending between a proximal end and a distal end, said distal end being releasably engageable to said first anchor when engaged to the spinal column, said first extender including a passage extending at least partially therethrough and opening at said distal end, said first extender including an entry hole in one side thereof in communication with said passage and an elongated slot along another side thereof opposite said entry hole, said elongated slot being in communication with said passage and opening at said distal end;

a second anchor engageable to the spinal column;

a second extender extending between a proximal end and a distal end, said distal end being releasably engageable to said second anchor when engaged to the spinal column, said second extender including a passage extending at least partially theretbrough and opening at said distal end, said second extender including an elongated slot in one side thereof in communication with said passage, said elongated slot of said second extender being alignable with said elongated slot of said first extender;

a connecting member positionable through said entry hole of said first extender and into a position extending between said passages of said first and second extenders through said elongated slots of said first and second extender, wherein:

at least one of said extenders includes an engaging member defining said passage, said engaging member being removably engageable with a respective one of said first and second anchors, said at least one extender further including an actuator positioned about said engaging member and movable therealong to bias said engaging member into engagement with said respective anchor;

said engaging member includes a pair of opposite legs separated from one another by a pair of opposite slots, said slots each including a proximal terminal end spaced distally from a proximal end of said engaging member;

said actuator includes a tubular body positionable over said engaging member, said tubular body defining at least one slot extending therealong aligned wit one of said slots of said engaging member to form said elongated slot of said at least one extender; and said actuator defines said entry hole in a side thereof opposite said at least one slot of said actuator, said entry hole being offset proximally of said proximal terminal ends of said slots of said engaging member.

3. The system of claim 2, wherein said engaging member includes an entry hole in communication with said passage and spaced proximally of said proximal terminal ends of said slots of said engaging member, said entry hole of said engaging member being aligned with said entry hole of said actuator.

4. A spinal surgical system, comprising:

at least three anchors engageable to the spinal column, each of said anchors including a receiver member;

at least three extenders positionable adjacent one another and engageable to respective ones of said at least three anchors, each of said at least three extenders extending along a longitudinal axis proximally from said respective anchor when engaged thereto, each said at least three extenders further defining a passage opening along at least a portion of a length of the respective extender adjacent at least at a distal end of said respective extender and into said receiver member of said respective anchor when engaged thereto, at least one of said extenders including an opening adjacent a proximal end thereof in a side thereof opposite the other of the at least three extenders;

a connecting member positioned through said opening between said at least three extenders transversely to said longitudinal axes of said extenders and in said passages thereof, said connecting member being movable in said passages and along said at least three extenders into said receiver members of said anchors, wherein:

at least one of said extenders includes an engaging member defining said passage, said engaging member being removably engageable with said receiver member, said at least one extender further including an actuator positioned about said engaging member and movable therealong to bias said engaging member into engagement with said receiver member;

said engaging member includes a pair of opposite legs separated from one another by a pair of opposite slots, said slots each including a proximal terminal end spaced distally from a proximal end of said engaging member;

said actuator includes a tubular body positionable over said engaging member, said tubular body defining at least one slot extending therealong alignable with one of said slots of said engaging member; and said actuator defines an entry hole in a side thereof opposite said at least one slot of said tubular body, said entry hole being aligned with the other of said slots of said engaging member to form said opening.

5. The system of claim 4, wherein said entry hole is aligned axially with said proximal terminal end of the other of said slots of said engaging member.

6. A spinal surgical system, comprising:

at least three anchors engageable to the spinal column, each of said anchors including a receiver member;

at least three extenders positionable adjacent one another and engageable to respective ones of said at least three anchors, each of said at least three extenders extending along a longitudinal axis proximally from said respective anchor when engaged thereto, each said at least three extenders further defining a passage opening along at least a portion of a length of the respective extender adjacent at least at a distal end of said respective extender and into said receiver member of said respective anchor when engaged thereto, at least one of said extenders including an opening adjacent a proximal end thereof in a side thereof opposite the other of the at least three extenders;

a connecting member positioned through said opening between said at least three extenders transversely to said longitudinal axes of said extenders and in said passages thereof, said connecting member being movable in said passages and along said at least three extenders into said receiver members of said anchors, wherein:

at least one of said extenders includes an engaging member defining said passage, said engaging member being removably engageable with said receiver member, said at least one extender further including an actuator positioned about said engaging member and movable therealong to bias said engaging member into engagement with said receiver member;

said engaging member includes a pair of opposite legs separated from one another by a pair of opposite slots, said slots each including a proximal terminal end spaced distally from a proximal end of said engaging member;

said actuator includes a tubular body positionable over said engaging member, said tubular body defining at least one slot extending therealong alignable with one of said slots of said engaging member; and said engaging member includes an entry hole in a side thereof spaced proximally of said proximal terminal end of the other of said slots of said engaging member.

7. The system of claim 6, wherein said actuator includes an entry hole in a side thereof alignable with said entry hole of said engaging member to form said opening.

8. A spinal surgical system, comprising:

a first anchor engageable to bony structure;

a first extender extending between a proximal end and a distal end, said distal end being releasably engageable to said first anchor when engaged to bony structure, said first extender including a passage extending at least partially therethrough and opening at said distal end, wherein said first extender includes:

an engaging member removably engageable with said first anchor, said engaging member defining said passage and including a pair of opposite slots opening into said passage, said opposite slots each extending to a proximal terminal end spaced distally from a proximal end of said engaging member;

an actuator including a tubular body positioned about said engaging member, said tubular body defining at least one slot extending therealong aligned with one of said opposite slots of said engaging member, said engaging member further including an entry hole in a side thereof opposite said at least one slot, said entry hole being substantially aligned with said proximal terminal end of said opposite slot of said engaging member aligned with said at least one slot of said engaging member;

a second anchor engageable to bony structure;

a second extender extending between a proximal end and a distal end, said distal end being releasably engageable to said second anchor when engaged to bony structure, said second extender including a passage extending at least partially therethrough and opening at said distal end, said second extender including opposite elongated slots in opposite sides thereof in communication with said passage, said elongated slots of said second extender being alignable with said elongated slots of said first extender; and a connecting member positioned between said passages of said first and second extenders, wherein when positioned between said passages of said first and second extenders said connecting member includes a length sized to project through oppositely facing elongated slots of said first and second extenders as said connecting member is moved along said first and second extenders toward said first and second anchors.

9. The system of claim 8, further comprising a third anchor and a third extender extending between a proximal end and a distal end, said distal end being releasably engageable to said third anchor when engaged to bony structure on a side of said second anchor opposite said first anchor, said third extender including a passage extending at least partially therethrough and opening at said distal end, said third extender including opposing slots therealong in communication with said passage and opening at said distal end of said third extender.

10. The system of claim 9, wherein said connecting member is positionable between said passages of said first, second and third extenders through said elongated slots of said first, second and third extenders.

11. The system of claim 9, wherein said of said first, second and third extenders are pivotal relative to at least a portion of said respective anchor when engaged thereto.

* * * * *

UNITED STATES PATENT AND TRADEMARK OFFICE
CERTIFICATE OF CORRECTION

PATENT NO. : 7,465,306 B2 Page 1 of 1
APPLICATION NO. : 10/918835
DATED : December 16, 2008
INVENTOR(S) : John D. Pond, Jr. et al.

It is certified that error appears in the above-identified patent and that said Letters Patent is hereby corrected as shown below:

At Claim 11, Column 26, Line 36, please delete "said of."

Signed and Sealed this

Twenty-fourth Day of November, 2009

David J. Kappos
*Director of the United States Patent and Trademark Office*